US010722505B2

(12) United States Patent
Bassissi et al.

(10) Patent No.: US 10,722,505 B2
(45) Date of Patent: *Jul. 28, 2020

(54) SUBSTITUTED 2,4 DIAMINO-QUINOLINE AS NEW ANTICANCER AGENTS

(71) Applicant: GENOSCIENCE PHARMA, Marseilles (FR)

(72) Inventors: Firas Bassissi, Marseilles (FR); Antoine Beret, Marseilles (FR); Sonia Brun, Aix-en-Provence (FR); Jérôme Courcambeck, Marseilles (FR); Clarisse Dubray, Aix-en-Provence (FR); Gregory Nicolas, Marseilles (FR); Philippe Halfon, Marseilles (FR)

(73) Assignee: GENOSCIENCE PHARMA, Marseilles (FR)

( * ) Notice: Subject to any disclaimer, the term of this patent is extended or adjusted under 35 U.S.C. 154(b) by 65 days.

This patent is subject to a terminal disclaimer.

(21) Appl. No.: 15/543,504

(22) PCT Filed: Oct. 26, 2015

(86) PCT No.: PCT/IB2015/002438
§ 371 (c)(1),
(2) Date: Jul. 13, 2017

(87) PCT Pub. No.: WO2016/067112
PCT Pub. Date: May 6, 2016

(65) Prior Publication Data
US 2019/0314359 A1    Oct. 17, 2019

Related U.S. Application Data

(60) Provisional application No. 62/073,325, filed on Oct. 31, 2014.

(51) Int. Cl.
A61K 31/506    (2006.01)
A61K 31/4545   (2006.01)
A61P 35/00     (2006.01)
A61K 9/127     (2006.01)
A61K 9/14      (2006.01)
C07D 401/04    (2006.01)
C07D 401/14    (2006.01)

(52) U.S. Cl.
CPC ........ *A61K 31/4545* (2013.01); *A61K 9/1273* (2013.01); *A61K 9/14* (2013.01); *A61K 31/506* (2013.01); *A61P 35/00* (2018.01); *C07D 401/04* (2013.01); *C07D 401/14* (2013.01)

(58) Field of Classification Search
None
See application file for complete search history.

(56) References Cited

U.S. PATENT DOCUMENTS

2014/0200227 A1* 7/2014 Xue ................ A61K 31/444
514/255.05

OTHER PUBLICATIONS

Abbas et al., New quinoline/chalcone hybrids as anti-cancer agents: Design, synthesis, and evaluations of cytotoxicity and PI3K inhibitory activity, Bioorganic Chemistry, 82:360-377 (2019).
Benfodda et al., Synthesis, Anticancer Activity and Computational SAR Analysis of Acylsulfonylpiperazines Derivatives, Medicinal Chemistry, 7:9 p. 257-267 (2017).
Cherian et al., Chemical Modulation of the Biological Activity of Reutericyclin: a Membrane-Active Antibiotic from Lactobacillus reuteri, Scientific Report, 4:04721 (2014).
Viswas et al., Design and synthesis of 4-piperazinyl quinoline derived urea/thioureas for anti-breast cancer activity by a hybrid pharmacophore approach, J Enz Inhibition & Med Chem, 34(1):620-830 (2019).
Wang et al., Design, synthesis and biological evaluation of novel 4-anlinoquinazoline derivatives as EGFR inhibitors with the potential to inhibit the gefitinib-resistant nonsmall cell lung cancers, J Enz Inhibition & Med Chem, 34(1):203-217 (2019).
Xiao et al., Design, synthesis, and antitumor evaluation of quinoline-imidazole derivatives, Arch Pharm., 351: e1700407 (2018).
Zhang et al., Design, Synthesis and Biological Evaluation of a Novel Series of Indole-3-Carboxamide Derivatives for Cancer Treatment as EGFR Inhibitors, Letters in Drug Design & Discovery, 15(1):70-83 (2018).
Chong et al., Design of N-Benzoxaborole Benzofuran GSK8175—Optimization of Human PK Inspired by Metabolites of a Failed Clinical HCV Inhibitor, Journal of Medicinal Chemistry, 62(7):3254-3267 (2019).
Kundu, Discovery and Mechanistic Study of Tailor-Made Quinoline Derivatives as Topoisomerase 1 Poisons with Potent Anticancer Activity, J. Med. Chem., 62(7):3428-3446 (2019).
Peese et al., 5,6,7,8-Tetrahydro-1,6-naphthyridine Derivatives as Potent HIV-1-Integrase-Allosteric-Site Inhibitors, J. Med. Chem., 62(3):pp. 1348-1361 (2019).
Schnute et al., Discovery of 3-Cyano-N-(3-(1-isobutyrylpiperidin-4-yl)-1-methyl-4-(trifluoromethyl)-1H-pyrrolo[2,3-b] pyridin-5-yl)benzamide: A Potent, Selective, and Orally Bioavailable Retinoic Acid Receptor-Related Orphan Receptor C2 Inverse Agonist, J. Med. Chem., 61(23):pp. 10415-10439 (2018).
Madak et al., Design, Synthesis, and Biological Evaluation of 4-Quinoline Carboxylic Acids as Inhibitors of Dihydroorotate Dehydrogenase, J. Med. Chem., 61(12):5162-5186 (2018).
Yang et al., Structure-activity relationship of rubiscolins as 6 opioid peptides, Petitdes, 24:503-508 (2003).

(Continued)

*Primary Examiner* — Samantha L Shterengarts
(74) *Attorney, Agent, or Firm* — Browdy and Neimark, PLLC

(57) ABSTRACT

The present invention relates to novel 2-primary amino-4-secondary amino-quinoline derivatives, their manufacture, pharmaceutical compositions comprising them and their use as medicaments. The active compounds of the present invention are useful for the treatment and prevention of proliferative neoplastic and non-neoplastic diseases.

24 Claims, 6 Drawing Sheets

(56) References Cited

OTHER PUBLICATIONS

Chhabra et al., A review of drug isomerism and its significance, International Journal of Applied and Basic Medical Research, 3(1):16-18 (2013).
Scott, Stereoisomers and Drug Toxicity the Value of Single Stereoisomer Therapy, Drug Safety, 8(2):149-159 (1993).
Gandhi et al., Drug Stereochemistry: A Prodigy for Pharmacology and Drug Development, Current Drug Discovery Technologies, 16:1-9 (2019).

* cited by examiner

SUBSTITUTED 2,4 DIAMINO-QUINOLINE AS NEW ANTICANCER AGENTS

FIELD OF THE INVENTION

The present invention relates to novel 2-primary amino-4-secondary amino-quinoline derivatives, their manufacture, pharmaceutical compositions comprising them and their use as medicaments. The active compounds of the present invention are useful for the treatment and prevention of proliferative neoplastic and non-neoplastic diseases.

BACKGROUND OF THE INVENTION

The drug discovery of new anticancer agents has recently moved from cell-based assay to a more focused in vitro approach on well characterized, isolated and transfection assisted expressed proteins of druggable targets. This protein(s) targeted drug discovery paradigm is well described in the art with the large effort produced in the drug discovery field of the rational design of human kinase inhibitors allowing to explore the human kinome. Indeed, human kinase could be mutated and kinase deregulation usually take place in malignant transformation, growth and the ultimate metastasis evolution of human cancers. This kinase implication in the development and the proliferation of cancers is well establish in for example leukemia, lymphoma, non-small-cell lung cancer, melanoma, colon, breast, kidney, hepatocarcinoma . . . . Nowadays, despite this large effort to target human kinase dysfunctions in some cancers, the clinical breakthrough of the use of kinase inhibitor in anti-cancer therapy is not obviously associated with curing or remission, and several cancers seems to remain naturally resistant to the clinical use of kinase inhibitors (e.g. hepatocellular carcinoma). Moreover, the kinase inhibitors can select in vivo some mutated and resistant strains or the transformed cells can find equally compensating pathways. In this context, we decided to take into account the whole cell compartment and a cellular culture environment with the development of an unbiased phenotypic cellular screening assay. Moreover, the molecular understanding and the molecular description of cellular transformation, cancer growth and metastasis evolution is still remain in constant development, with for example the recent description of the cancer stem cells (CSCs) concept or tumor initiating cells (TICs). Unexpected effects in cellular screening may suggest other targets or specific interactions for the discovery of a new druggable target. Therefore, the development of new anticancer agents still remains a unique challenge with unpredictable outcome and a place for the discovery of new and innovative compounds.

The inventors have prepared a new series of diversity oriented of 2-primary amino-2-secondary amino-arylquinoline compounds library which was screened against a panel of human cancer cell lines (MOLM14, KG-1, MV4-11, A375, HCT116, HepG2, huh-7, MDA-MB-231, CAKI-1, 786-O) and patient-derived cancer primary cells allowing to discover novel anticancer agents. Moreover, this class of compounds shows equally an additional activity against human cancer stem cells (CSCs) which are widely incriminated in the recurrence and the relapse of cancers after anti-cancer therapy. A well describe in the art ALDH assay was used as cancer stem cell functional marker to describe the activity against CSCs (Greve, B. et al. Cytometry A 2012 (81) 284-293, Liu, S. et al. PLoS One 2013 (25) e81050, Ran, D. et al. Exp. Hematol. 2009 (37) 1423-1434, Cheung, A. M. et al. Leukemia 2007 (21) 1423-1430, Pearce, D. J. et al. Stem Cells 2005 (23) 752-760).

Therefore, it is an object of the present invention to provide active agents for preventing or inhibiting cell proliferation in a variety of organisms, and to provide methods for their synthesis.

It is another object of the present invention to provide a pharmaceutical composition comprising a therapeutically effective amount of active agents of the invention, alone nor in combination with other active agents, and a pharmaceutically acceptable adjuvant, diluent or carrier.

It is another object of the present invention to provide active agents for use in therapy.

It is another object of the present invention to provide a method for the treatment and/or prevention of a proliferative and/or neoplastic disease.

It is another object of the present invention to provide a method for inhibiting the growth or differentiation of a Cancer Stem Cell (CSC), a tumor initiating cell, a mesenchymal-like cell associated with cancer, a mesenchymal cancerous cell, or a mesenchymal cell.

SUMMARY OF THE INVENTION

The present invention provides compound of formula (I)

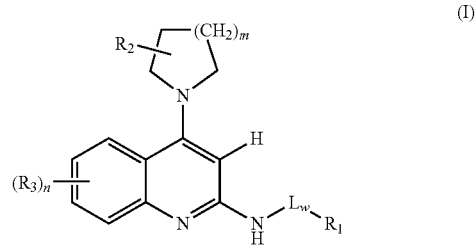

Wherein
- $R_1$ can be chosen from a C6-C10 aryl substituted or not by $R_9$; a heteroaryl 5 to 8-membered ring comprising 1, 2, or 3 heteroatoms selected from O, N and S substituted or not by $R_9$; a fused heteroaryl as defined comprising from 8 to 13 atoms including 1, 2, 3, 4 heteroatoms selected from O, N and S and comprising at least 2 carbon atoms substituted or not by $R_9$;
- $L_w$ can be chosen from an optionally substituted (C1-C10) alkyl; a (C1-C10) alkyl linear or branched substituted by $R_4$; an optionally substituted (C3-C10) cycloalkyl; an optionally substituted (C5-C10) cycloalkenyl; an optionally substituted (C3-C10) alkenyl; an optionally substituted (C3-C10) alkynyl; C=O; SO; $SO_2$; (C=O)—$NR_8$; (C=O)—O; (C=O)—O—(C1-C4) alkyl; $SO_2$—$NR_8$; $NR_8$; wherein $R_4$ can be chosen from H; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; an optionally substituted (C6-C10) aryl; an heteroaryl 5 to 8-membered ring or a fused heteroaryl as defined comprising from 8 to 13 atoms including 1, 2, 3, 4 heteroatoms selected from O, N and S and comprising at least 2 carbon atoms substituted or not with one or more substituent groups independently selected from hydrogen, halogen atom, (C1-C10) alkyl substituted with by one or more halogens atom(s), (C1-C10) alkoxy, hydroxyl, cyano, nitro, carboxy, $NR_8R_8'$, a 4 to 9-membered ring saturated or unsaturated comprising 1, 2 or until 3 heteroatoms independently selected from O, N and S;

$R_2$ is selected from $NR_5R_6$;

$R_3$ can be chosen from a hydrogen atom; a halogen atom; a (C1-C10) alkyl linear or branched substituted or not by one or more halogen atom(s), hydroxyl, alkoxy, —$NR_5R_6$; a (C2-C10) alkenyl; a (C2-C10) alkynyl; a (C3-C10) cycloalkyl; a (C5-C10) cycloalkenyl; a (C8-C10) cycloalkynyl; a (C1-C10) alkoxy; a hydroxyl; a nitro; a cyano; a $NR_5R_6$; a O—($R_7$); a (CO)—$R_7$; a (CO)—O—$R_7$; a (CO)—$NR_5R_6$; a O—(CO)—$R_7$; a O—(CO)—$NR_5R_6$; a $NR_5$—(CO)—$R_7$; a $NR_5$—(CO)—$OR_7$; a $NR_5$—(CO)—$NR_5R_6$; a —(O—$CH_2CH_2$—)$_m$—$OR_{11}$; a —(O—$CH_2CH_2$—)$_m$—$NR_{11}R_{11'}$; a $SO_2$—$R_7$; a $NR_5$—$SO_2$—$R_7$; a $SO_2$—$NR_5R_6$; a $NR_5$—(C2-C6)-alkyl-$NR_5R_6$; an optionally substituted aryl; an optionally substituted benzyl; an optionally substituted heteroaryl from 5 to 8-membered ring comprising 1, 2, or 3 heteroatoms selected from O, N and S; an optionally substituted fused heteroaryl as defined comprising from 8 to 13 atoms including 1, 2, 3, 4 heteroatoms selected from O, N and S and comprising at least 2 carbon atoms; an optionally substituted heterocyclyl from 4 to 9-membered ring saturated or unsaturated comprising 1, 2 or until 3 heteroatoms independently selected from O, N and S;

$R_5$ and $R_6$ can be independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; a (CO)—$R_7$, a (CO)—O—$R_7$; a (CO)—$NR_8R_8'$; a $SO_2$—$R_7$; a $SO_2$—$NR_8R_8'$; a (C1-C10) alkyl substituted with $NR_8R_8'$; a (C3-C10) cycloalkyl substituted with $NR_8R_8'$; an optionally substituted aryl; an optionally substituted benzyl; an optionally substituted heteroaryl 5 to 8-membered ring comprising 1, 2, or 3 heteroatoms selected from O, N and S; an optionally substituted heterocyclyl from 4 to 9-membered ring saturated or unsaturated comprising 1, 2 or until 3 heteroatoms independently selected from O, N and S; or $R_5$ and $R_6$ can be linked together with the nitrogen atom to which they are covalently linked to form a heterocyclyl group forming a 4 to 9-membered ring which may contain additional 1, 2, or 3 heteroatoms selected from O, N and S;

$R_7$ and $R_{7'}$ can be independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; a C1-C10 linear or branched alkyl substituted with $NR_8R_8'$; an optionally substituted (C6-C10) aryl; an optionally substituted benzyl; an optionally substituted heteroaromatic 5 to 8-membered ring comprising 1, 2, or 3 heteroatoms selected from O, N and S;

$R_8$ and $R_{8'}$ can be independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; or $R_8$ and $R_3$, can be linked together with the nitrogen atom to which they are covalently linked to form a heterocyclyl group forming a 4 to 9-membered ring which may contain additional 1, 2, or 3 heteroatoms selected from O, N and S;

$R_9$ can be independently selected from a hydrogen; a halogen atom; an optionally substituted (C1-C10) alkyl; an (C1-C10) alkyl linear or branched substituted by one or more halogen atom(s), a hydroxyl, an alkoxy; an optionally substituted (C2-C10) alkenyl; an optionally substituted (C2-C10) alkynyl; an optionally substituted (C3-C10) cycloalkyl; an optionally substituted (C5-C10) cycloalkenyl; an optionally substituted (C8-C10) cycloalkynyl; an optionally substituted (C1-C10) alkoxy; a hydroxyl; a nitro; a cyano; a $NR_5R_6$; a (CO)—$R_7$; a (CO)—O—$R_7$; a (CO)—$NR_5R_6$; a O—(CO)—$R_7$; a O—(CO)—$NR_5R_6$; a $NR_5$—(CO)—$R_7$; a $NR_5$—(CO)—$OR_7$; a $NR_5$—(CO)—$NR_5R_6$; a $SO_2$—$R_7$; a $NR_5$—$SO_2$—$R_7$; a $SO_2$—$NR_5R_6$; a (C1-C10) alkyl substituted with $NR_5R_6$; a $NR_5$—(C2-C10)-alkyl-$NR_5R_6$; a —(O—$CH_2CH_2$—)$_m$—$OR_{11}$; a —(O—$CH_2CH_2$—)$_m$—$NR_{11}R_{11'}$; an optionally substituted (C6-C10) aryl; an optionally substituted benzyl; an optionally substituted heteroaryl 5 to 8-membered ring comprising 1, 2, or 3 heteroatoms selected from O, N and S; an optionally substituted heterocyclyl group forming a 4 to 9-membered ring which may contain 1, 2, or 3 heteroatoms selected from O, N and S; a —$NR_5R_{10}$; a —O—$R_{10}$;

$R_{10}$ can be independently chosen from a hydrogen; a (C6-C12)-aryl substituted or not by $R_{12}$; a benzyl substituted or not by $R_{12}$; a heteroaryl from 5 to 8-membered ring comprising 1, 2, or 3 heteroatoms selected from O, N and S substituted or not by $R_{12}$; a fused heteroaryl defined as comprising from 8 to 13 atoms including 1, 2, 3, 4 heteroatoms selected from O, N and S and comprising at least 2 carbon atom substituted or not by $R_{12}$; a heterocyclyl forming a 4 to 9-membered ring which may contain 0, 1, 2, or 3 heteroatoms selected from O, N and S substituted or not by $R_{12}$;

$R_{11}$ and $R_{11'}$ can be independently chosen from a hydrogen atom; an optionally substituted (C2-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; an (C2-C10) alkyl linear or branched substituted or not by one or more halogen atom(s); or $R_{11}$ and $R_{11'}$ can be linked together with the nitrogen atom to which they are covalently linked to form a heterocyclyl group forming a saturated or unsaturated 4 to 9-membered ring which may contain additional 1, 2, or 3 heteroatoms selected from O, N and S;

$R_{12}$ can be chosen from a hydrogen atom; a halogen atom; a (C1-C10) alkyl linear or branched substituted or not by one or more halogen atom(s), hydroxyl, alkoxy, $NR_{11}R_{11'}$; a (C2-C10) alkenyl; a (C2-C10) alkynyl; a (C3-C10) cycloalkyl; a (C5-C10) cycloalkenyl; a (C8-C10) cycloalkynyl; a (C1-C10) alkoxy; a hydroxyl; a nitro; a cyano; a $NR_{11}R_{11'}$; a O—($R_7$); a (CO)—$R_7$; a (CO)—O—$R_7$; a (CO)—$NR_{11}R_{11'}$; a O—(CO)—$R_7$; a O—(CO)—$NR_{11}R_{11'}$; a $NR_{11}$—(CO)—$R_7$; a $NR_{11}$—(CO)—$OR_{11'}$; a $NR_{11}$—(CO)—$NR_{11}R_{11'}$; a —(O—

CH$_2$CH$_2$—)$_m$—OR$_{11}$; a —(O—CH$_2$CH$_2$—)$_m$—NR$_{11}$R$_{11'}$; a SO$_2$—R$_7$; a NR$_5$—SO$_2$—R$_7$; a SO$_2$—NR$_{11}$R$_{11'}$; a NR$_{11}$—(C2-C6)-alkyl-NR$_{11}$R$_{11'}$; an optionally substituted aryl; an optionally substituted benzyl; an optionally substituted heteroaryl from 5 to 8-membered ring comprising 1, 2, or 3 heteroatoms selected from O, N and S; an optionally substituted fused heteroaryl as defined comprising from 8 to 13 atoms including 1, 2, 3, 4 heteroatoms selected from O, N and S and comprising at least 2 carbon atoms; an optionally substituted heterocyclyl from 4 to 9-membered ring saturated or unsaturated comprising 1, 2 or until 3 heteroatoms independently selected from O, N and S;

n can represent an equal integer which can have any one of the values 0, 1, 2, 3 or 4;

m can represent an equal integer which can have any one of the values 1, 2 or 3;

w can represent an equal integer which can have any one of the values 0 or 1;

Wherein the term "optionally substituted" means optionally substituted with one or more substituents independently chosen from an halogen atom, a (C1-C10) alkyl linear or branched substituted or not by one or more halogen atom(s), a (C2-C10) alkenyl linear or branched substituted or not by one or more halogen atom(s), a (C2-C10) alkynyl linear or branched substituted or not by one or more halogen atom(s), a (C3-C10) cycloalkyl substituted or not by one or more halogen atom(s), a (C5-C10) cycloalkenyl substituted or not by one or more halogen atom(s), a (C8-C10) cycloalkynyl substituted or not by one or more halogen atom(s), a (C1-C10) alkoxy, a hydroxyl, a cyano, a nitro, a NR$_8$R$_{8'}$— (with R$_8$ and R$_{8'}$ as described above);

and any pharmaceutically acceptable salt, solvate, isomers, stereoisomers or mixtures of stereoisomers, solvate or prodrug thereof.

In some specific embodiments, the invention provides a compound chosen from:

2-(4-chlorophenylamino)-4-(4-tert-butylaminopiperidin-1-yl)-quinoline of Formula (Ia) (1-5)

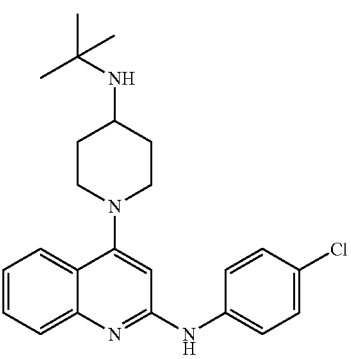

(Ia)

2-(4-chlorobenzylamino)-4-(4-tert-butylaminopiperidin-1-yl)-quinoline of Formula (Ib) (2-2)

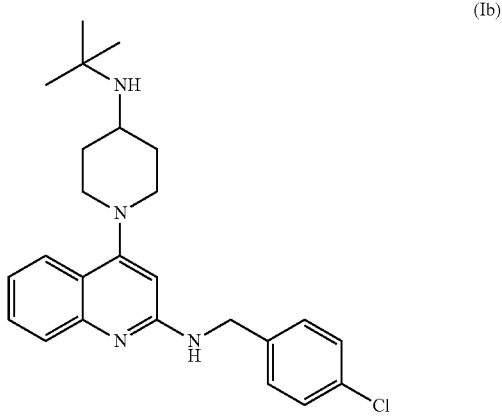 [SMILES: CC(C)(C)NC1CCN(c2cc(NCc3ccc(Cl)cc3)nc3ccccc23)CC1]

(Ib)

2-[3-methyl-4-(pyrimidin-2-ylamino)phenylamino]-4-(4-tert-butylaminopiperidin-1-yl)-quinoline (3-4) of Formula (Ic)

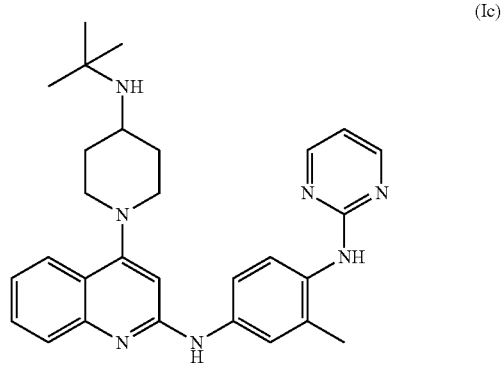 [SMILES: Cc1cc(Nc2cc(N3CCC(NC(C)(C)C)CC3)c3ccccc3n2)ccc1Nc1ncccn1]

(Ic)

2-{4-[4-(pyridin-3-yl)-2-pyrimidinamino]-3-methylphenylamino}-4-(4-tert-butylaminopiperidin-1-yl)-quinoline (4-2) of Formula (Id)

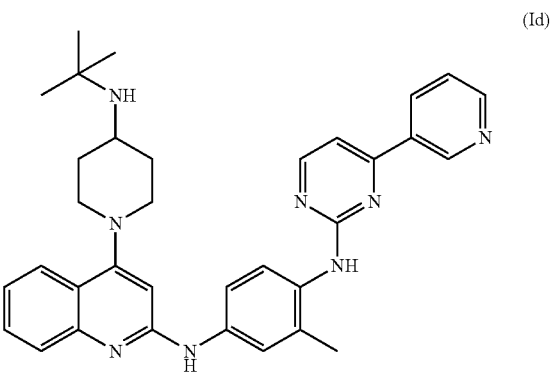 [SMILES: Cc1cc(Nc2cc(N3CCC(NC(C)(C)C)CC3)c3ccccc3n2)ccc1Nc1nccc(-c2cccnc2)n1]

(Id)

or a pharmaceutically acceptable salt, solvate or prodrug thereof.

In some other specific embodiments, the invention provides a compound chosen from 2-(4-chlorophenylamino)-4-(4-tert-butylaminopiperidin-1-yl)-quinoline hydrochloride salt (1-6), 2-(4-chlorobenzylamino)-4-(4-tert-butylaminopiperidin-1-yl)-quinoline hydrochloride salt (2-3), 2-[3-methyl-4-(pyrimidin-2-ylamino)phenylamino]-4-(4-tert-butylaminopiperidin-1-yl)-quinoline hydrochloride salt (3-5), 2-{4-[4-(pyridin-3-yl)-2-pyrimidinamino]-3-methyl-phenylamino}-4-(4-tert-butylaminopiperidin-1-yl)-quinoline hydrochloride salt (4-3).

In another aspect, the invention provides a pharmaceutical composition that can comprise a therapeutically effective amount of a compound according to the above, or a pharmaceutically acceptable salt, solvate or prodrug thereof, and a pharmaceutically acceptable adjuvant, diluent or carrier.

In some particular embodiments, the pharmaceutical composition of the invention can further comprise one or more anti-neoplastic agents.

In some particular embodiments, the pharmaceutical composition according to the above can comprise a therapeutically effective amount of the compound of the invention which can be formulated or co-formulated in nanoparticles.

In some specific embodiments of the pharmaceutical composition of the invention, the nanoparticles can comprise a lisosomal biodegradable composition.

In some specific embodiments of the pharmaceutical composition of the invention, the nanoparticles can comprise a biocompatible polymer or copolymer.

In some specific embodiments of the pharmaceutical composition of the invention, the nanoparticles can be associated covalently or non-covalently with a polyethylene glycol (PEG).

In some specific embodiments of the pharmaceutical composition of the invention, the nanoparticles can have an average size of from about 80 to about 600 nm.

In some specific embodiments of the pharmaceutical composition of the invention, the nanoparticle can be a targeted nanoparticle containing a signaling motif.

In some specific embodiments, the nanoparticles can comprise a polymeric biodegradable composition.

In some particular specific embodiments, the polymer can be based on Poly (DL-Lactic-co-glycolic acid) that can have a molecular weight from 7 to 240 kDa; or a copolymer of polylactic acid (PLA) and polyglycolic acid (PGA) where the molecular ratio can be between 95:5 and 50:50.

In some specific embodiments of the pharmaceutical composition of the invention, the nanoparticles can comprise an item chosen from PLGA nanoparticules, PLGA-PEG nanoparticules (block type AB, BA, ABA or BAB, where A=PLGA and B=PEG) and targeted nanoparticules.

In some specific embodiments of the pharmaceutical composition of the invention, the nanoparticles can comprise an item chosen from liposomes.

In some embodiments, the pharmaceutical composition of the invention can be suitable for slow- or sustained-release.

In some specific embodiments, the pharmaceutical composition of the invention can be suitable for oral-, parenteral-, ocular-, transdermal-, nasal-administration, or for inhalation.

In some specific embodiments of the pharmaceutical composition of the invention, the active compound of the invention can be associated with at least one therapeutically active anti-cancer agent.

In some specific embodiment, the pharmaceutical composition of the invention can comprise a combination of a therapeutically effective amount of a compound of the invention and a therapeutically effective amount of one or more anti-neoplastic agents, wherein the components constituting said combination can be for simultaneous, separate or sequential use in cancer therapy.

In specific embodiments of the pharmaceutical composition of the invention, the anti-neoplastic agent can be chosen from the group consisting of everolimus, chloroquine, hydroxychloroquine, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrme, rubitecan, tesmilifene, oblimersen, ticilimumab, ipilimumab, gossypol, Bio 111, 131-I-TM-601, ALT-110, BIO 140, CC 8490, cilengitide, gimatecan. IL13-PE38QQR, TNO 1001, IPdR1 KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-disodium salt heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolyl]-quinolone, vatalanib, AG-013736, AVE-0005, the acetate salt of [D-Ser(But)$_6$, Azgly$_{10}$](pyro-Glu-His-Trp-Ser-Tyr-D-Ser(But)-Leu-Arg-Pro-Azgly-NH$_2$ acetate, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevec, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, 1M862, angiostatin, vitaxin, droloxifene, idoxyfene, spironolactone, finasteride, cimitidine, trastuzumab, denileukin diftitox, gefitinib, bortezimib, paclitaxel, irinotecan, topotecan, doxorubicin, docetaxel, vinorelbine, bevacizumab (monoclonal antibody) and erbitux, cremophor-free paclitaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, epoetin alfa and darbepoetin alfa, ipilumumab, vemurafenib, FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, a mTOR inhibitor, an AKT inhibitor, a JAK/STAT inhibitor, a checkpoint-1 or 2 inhibitor, a focal adhesion kinase inhibitor, a Map kinase kinase (MEK) inhibitor, a VEGF trap antibody, and mixtures thereof.

In another aspect, the invention provides a method for the treatment and/or prevention of a proliferative and/or neoplastic disease, that can comprise the step of administering a therapeutically active amount of a compound of the invention, or a pharmaceutical composition comprising the same, to a human being or animal in need thereof.

In another aspect, the invention provides a method for inhibiting the growth or differentiation of a Cancer Stem Cell (CSC), a tumor initiating cell, a mesenchymal-like cell associated with cancer, a mesenchymal cancerous cell, or a mesenchymal cell that can comprise the step of administering a therapeutically active amount of a compound of the invention, or a pharmaceutical composition comprising the same, to a human being or an animal in need thereof.

In another aspect, the invention provides a compound for the treatment and/or prevention of a proliferative and/or neoplastic disease.

In another aspect, the invention provides a compound for inhibiting the growth or differentiation of a Cancer Stem Cell (CSC), a tumor initiating cell, a mesenchymal-like cell associated with cancer, a mesenchymal cancerous cell, or a mesenchymal cell.

BRIEF DESCRIPTION OF THE DRAWING

The above and other characteristics and advantages of the invention will be more readily apparent through the following examples, and with reference to the appended drawings, wherein.

DETAILED DESCRIPTION

Figure 1:
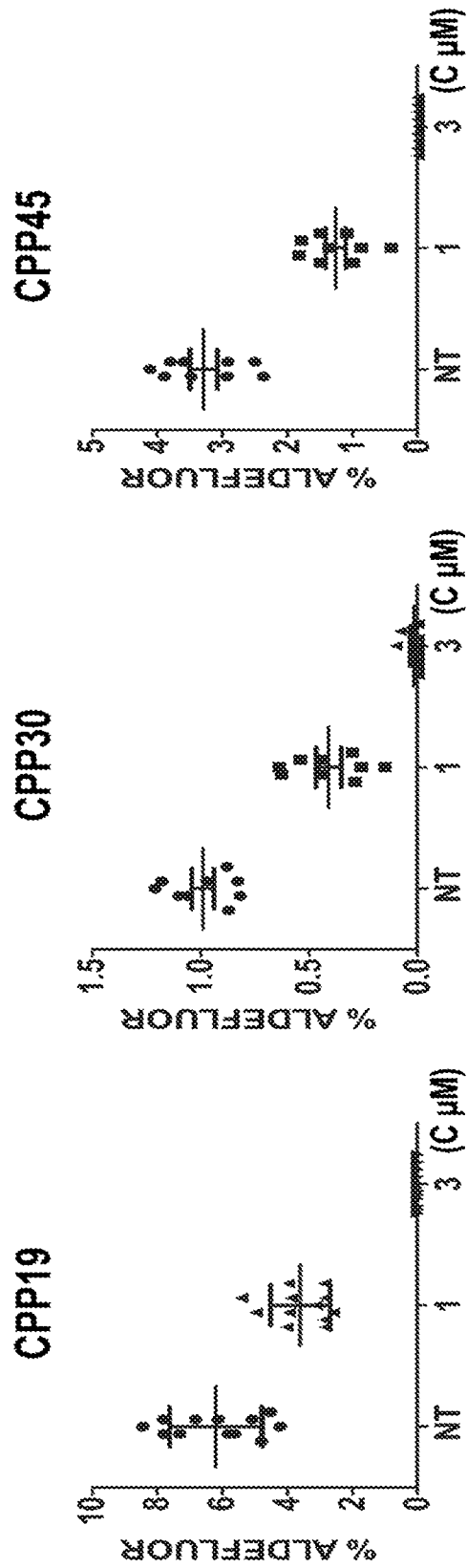
FIG. 1 shows the decrease of ALDH+ population cells in CRC patient derived cells (CPP19, CPP30 and CPP45) when treated by compound 2-3 (Aldefluor™ assay)

In the present description the term "alkyl", alone or in combination with other groups, refers to a branched or straight chain monovalent saturated aliphatic hydrocarbon radical of one to twenty carbon atoms, preferably one to sixteen carbon atoms, more preferably one to ten carbon atoms.

The term "lower alkyl", alone or in combination, signifies a straight-chain or branched-chain alkyl group with 1 to 6 carbon atoms ("$C_1$-$C_6$-alkyl"), preferably a straight or branched-chain alkyl group with 1 to 5 carbon atoms ("$C_1$-$C_5$-alkyl"), and particularly preferred a straight or branched-chain alkyl group with 1 to 3 carbon atoms ("$C_1$-$C_3$-alkyl"). Examples of straight-chain and branched lower alkyl groups are methyl, ethyl, propyl, isopropyl, butyl, isobutyl, tert-butyl, the isomeric pentyls, the isomeric hexyls, preferably methyl and ethyl and propyl and isopropyl and most preferred methyl.

The term "lower alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec-butoxy and tert-butoxy, preferably methoxy and ethoxy and isopropoxy and tert-butoxy most preferred methoxy and ethoxy.

The term "lower alkenyl" signifies a straight-chain or branched chain hydrocarbon residue comprising an olefinic bond and 2 to 6 carbon atoms ("$C_2$-$C_6$-alkenyl"), preferably 2 to 5 carbon atoms ("$C_2$-$C_5$-alkenyl"), particularly preferred 2 to 4 carbon atoms ("$C_2$-$C_4$-alkenyl"). Examples of lower alkenyl groups are ethenyl, 1-propenyl, 2-propenyl, isopropenyl, 1-butenyl, 2-butenyl, isobutenyl, 1-pentenyl, 2-pentenyl, 3-pentenyl, isopentenyl. Preferred examples are 2-propenyl, 2-butenyl and isopentenyl.

The term "lower alkynyl" signifies a straight-chain or branched chain hydrocarbon residue comprising an alkyne bond and 2 to 6 carbon atoms ("$C_2$-$C_6$-alkynyl"), preferably 2 to 5 carbon atoms ("$C_2$-$C_5$-alkynyl"), particularly preferred 2 to 4 carbon atoms ("$C_2$-$C_4$-alkynyl"). Examples of alkynyl groups are ethynyl, 1-propynyl, 2-propynyl, 1-butynyl, 3-butynyl, 4-butynyl, 1-but-2-yne, 1-pentynyl, pent-2-yn-1-yl, pent-3-yn-1-yl, pent-4-yn-1-yl, pent-2-yn-3-yl. Preferred examples are propyn-1-yl, propyn-3-yl, butyn-1-yl, butyn-3yl, butyn-4-yl, but-2-yn-1-yl.

The term "halogen" refers to fluorine, chlorine, bromine and iodine, with fluorine, chlorine and bromine being preferred.

The term "cycloalkyl" denotes a saturated carbocyclic group containing from 3 to 7 carbon atoms "$C_3$-$C_7$-cycloalkyl"), such as cyclopropyl, cyclobutyl, cyclopentyl, cyclohexyl or cycloheptyl. Preferred cycloalkyls are cyclopropyl, cyclopentyl and cyclohexyl.

The term "heterocyclic group" signifies a fully saturated or unsaturated but not fully unsaturated, for example 3 to 7 membered monocyclic groups or 7 to 11 membered fused bicyclic ring systems which have at least one heteroatom chosen from oxygen atom, nitrogen atom or sulfur atom. Each ring of the heterocyclic group can have at least one heteroatom chosen from nitrogen atoms, oxygen atoms and/or sulphur atoms. Preferred heterocyclic groups are pyrrolidine, piperidine, piperazine, tetrahydrofuran, bis-tetrahydrofuran and morpholine.

The term "carboxyl" means the group —COOH.

The term "heteroaryl" in general refers to an aromatic 5- or 11-membered ring which comprises at least one heteroatom and can in addition comprise one, two, three or four atoms chosen from nitrogen, oxygen and/or sulphur, such as pyridyl, pyrazinyl, pyrimidinyl, pyridazinyl, 2-oxo-1,2-dihydropyridinyl, oxadiazolyl, isoxazolyl, thiadiazolyl, triazolyl, tetrazolyl pyrazolyl, imidazolyl, thiophenyl, furanyl, oxazolyl, isothiazolyl, and thiazolyl. The term "heteroaryl" further refers to bicyclic aromatic or partly unsaturated groups comprising two 5- or 6-membered rings, in which one or both rings can contain one, two, three or four atoms chosen from nitrogen, oxygen or sulphur, such as quinolinyl, isoquinolinyl, cinnolinyl, pyrazolyl, imidazolyl, thiazolyl, thiophenyl, furanyl, oxazolyl, isothiazolyl, pyrazolo[1,5-a]pyridyl, imidazo[1,2-a] pyridyl, quinoxalinyl, quinazolyl, benzothiazolyl, benzotriazolyl, 1H-benzo[d]imidazole, benzo[d]isoxazolyl, benzo[d]isothiazolyl, benzo[c]isoxazolyl, benzo[c]isothiazolyl, indolyl, isoindolinyl, 6,7-dihydro-5H-pyrrolo[3,4-b]pyridinyl, 2,3-dihydro-1H-pyrrolo[3,4-c]pyridinyl, 6,7-dihydro-5 H-pyrrolo[3,4-d]pyrimidinyl, purinyl, indazolyl, indolizinyl, imidazo[1,2-a]pyridinyl, imidazo[1,5-a]pyridinyl, imidazo[1,5-a]pyrazinyl, imidazo[1,2-a]pyrazinyl, 1H-imidazo[4,5-b]pyrazinyl, pyrazolo[1,5-a]pyridinyl, pyrrolo[1,2-a]pyrimidinyl, pyrrolo[1,2-a]pyrazinyl, pyrrolo[1,2-c]pyrimidinyl, oxazolo[4,5-b]pyridinyl, oxazolo[4,5-c]pyridinyl, oxazolo[5,4-c]pyridinyl, oxazolo[5,4-b]pyridinyl, thiazolo[4,5-b]pyridinyl, thiazolo[4,5-c]pyridinyl, thiazolo[5,4-c]pyridinyl, thiazolo[5,4-b]pyridinyl, oxazolo[5,4-d]pyrimidinyl, oxazolo[4,5-d]pyrimidinyl, thiazolo[5,4-d]pyrimidinyl, thiazolo[4,5-d]pyrimidinyl, oxazolo[4,5-b] pyrazinyl, thiazolo[4,5-b]pyrazinyl, isoxazolo[4,5-b]pyrazinyl, isothiazolo[4,5-b]pyrazinyl, isoxazolo[4,5-d]pyrimidinyl, isothiazolo[4,5-d]pyrimidinyl, isoxazolo[5,4-d]pyrimidinyl, isothiazolo[5,4-d]pyrimidinyl, isoxazolo[5,4-b]pyridinyl, isothiazolo[5,4-c]pyridinyl, isoxazolo[5,4-c]pyridinyl, isothiazolo[4,5-c]pyridinyl, isoxazolo[4,5-c]pyridinyl, isoxazolo[4,5-b]pyridinyl, isoxazolo[4,3-d]pyrimidinyl, isthiazolo[4,3-d]pyrimidinyl, isoxazolo[3,4-d]pyrimidinyl, isothiazolo[3,4-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl, pyrido[2,3-b]pyrazinyl, pyrido[3,4-b]pyrazinyl, [1,2,3]triazolo[4,5-b]pyridinyl, [1,2,3]triazolo[4,5-c]pyridinyl, 3H-[1,2,3]triazolo[4,5-d]pyrimidinyl. Preferred heteroaryl groups are pyridyl, thiozolyl, isothiazolyl, oxazolyl, isoxazolyl, quinozolinyl, and pyrazinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, glutaric acid, cinnamic acid, mandelic acid, malic acid, methanesulfonic acid, ethanesulfonic acid, p-toluenesulfonic acid, benzenesulfonic acid, N-acetylcystein and the like. In addition, these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compounds of formula I can also be present in the form of zwitterions.

Particularly preferred pharmaceutically acceptable salts of compounds of formula I are the hydrochloride salts.

The compounds of formula I can also be solvated, e.g. hydrated. The solvation can be effectuated in the course of the manufacturing process or can take place e.g. as a consequence of hygroscopic properties of an initially anhydrous compound of formula I or II (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. As used herein, the terms "subject" or "patient" are used interchangeably. As used herein, the terms "subject" and "subjects" refer to an animal (e.g., birds, reptiles, and mammals), preferably a mammal including a non-primate (e.g., a camel, donkey, zebra, cow, pig, horse, goat, sheep, cat, dog, rat, and mouse) and a primate (e.g., a monkey, chimpanzee, and a human), and most preferably a human.

As used herein, the terms "therapies" and "therapy" can refer to any protocol(s), method(s), compositions, formulations, and/or agent(s) that can be used in the prevention, treatment, management, or amelioration of a disease, including viral or bacterial infections or symptoms associated therewith, cancers, etc. In certain embodiments, the terms "therapies" and "therapy" refer to biological therapy, supportive therapy, and/or other therapies useful in treatment, management, prevention, or amelioration of the different diseases known to one of skill in the art.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit can be exceeded when indicated. The daily dosage can be administered as a single dose or in divided doses, or for parenteral administration, it can be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, uses thereof in the compositions of the invention are contemplated. Supplementary active compounds can also be incorporated into the compositions. These compositions can be prepared by applying known techniques in the art as described in *Ansel's Pharmaceutical Dosage Forms and Drug Delivery Systems* (Tenth Edition) 2014, Edited by Loyd Allen, Howard C. Ansel, published by Wolters Kluwer Health and *Remington: The Science and Pratice of Pharmacy* (Twenty-second Edition) 2012, Edited by Loyd V. Allen, Published by Pharmaceutical Press, each of which is incorporated herein by reference.

As used herein, the terms "treat," "treatment," and "treating" refer in the context of administration of a therapy(ies) to a subject to treat a viral infection refer to one, two, three, four, five or more of the following effects resulting from the administration of a therapy or a combination of therapies: (i) the reduction or amelioration of the severity of a disease and/or a symptom associated therewith; (ii) the reduction in the duration of a disease and/or a symptom associated therewith; (iii) the regression of a disease and/or a symptom associated therewith; (iv) the reduction of the titer of a pathogen; (v) the reduction in organ failure associated with a disease; (vi) the reduction in hospitalization of a subject; (vii) the reduction in hospitalization length; (viii) the increase in the survival of a subject; (ix) the elimination of an infection; (x) the inhibition of the progression of an infection and/or a symptom associated therewith; (xi) the prevention of the spread of a virus from a cell, tissue or subject to another cell, tissue or subject; and/or (xii) the enhancement or improvement the therapeutic effect of another therapy.

"Prodrug" means a compound that undergoes conversion to the compound of the invention within a biological system. A prodrug is a chemical derivative inactive or less active than the drug itself. After administration and diffusion in the body, the prodrug derivative undergoes one or more metabolic processes that release the active drug. The conversion of the prodrug to the drug is generally carry out under the control of enzymatic processes (usually by metabolic means, e.g. hydrolysis, reduction or oxidation) and less frequently by classical chemical reactions during its diffusion in the body. The linkage between the carrier and the drug can be an, but not limited to, ester, amide, carbonate, carbamate, imine, acetal, ether (e.g. glucoro conjugation), oxydizable function and molecular system, reducible function and reducible molecular system, photoactivated function and photoactivated molecular system. For example, an ester prodrug of a compound containing a hydroxyl group may be convertible by hydrolysis in vivo to the parent molecule. Suitable esters of the compounds of the invention containing a hydroxyl group, are for example acetates, citrates, lactates, tartrates, malonates, oxalates, salicylates, propionates, succinates, fumarates, maleates, methylene-bis-6-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of the compound of the invention containing a carboxy group may be convertible by hydrolysis in vivo to the parent molecule (Examples of ester prodrugs are described by F. J. Leinweber, Drug Metab. Res. 1987, (18) pp 379, incorporated herein by reference). Similarly, an acyl prodrug of a compound containing an amino group may be convertible by hydrolysis in vivo to the parent molecule (examples of prodrugs for these and other functional groups, including amine, alcohol are described in *Prodrugs: Challenges and Rewards* (Parts 1 and 2); Ed V. Stella, R. Borchardt et al., Springer, 2007, and *Prodrugs and Targeted Delivery: Towards Better ADME Properties* Ed. J. Rautio, Seies Ed. R. Mannhold, H. Kubinyl, G. Folkers. Wiley-VCH 2011, each of which is incorporated herein by reference).

A prodrug carrier system is generally used in order to increase water or lipid solubility, reduce toxicity, increase chemical and biological stability of a sensitive compound, increase the circulating time in the body ($T_{1/2}$), increase the total drug exposure (AUC) and organ distribution (PK-PD profiling) and site specific targeting.

Material and Methods Relative to the Examples 1, 2, 3 and 4

Reagents and solvents were obtained from commercial suppliers and were used without further purification. Dry Methylene chloride was dried and distilled over $CaCl_2$ and stored over molecular sieves 4 Å under argon. Tetrahydrofuran was dried over sodium/benzophenone ketyl under argon and distilled prior to use. Flash chromatography purifications were performed on Merck silica gel (40-63 μM or 15-40 μM) as the stationary phase.

NMR spectra were recorded on Bruker Avance 300 MHz. Analytical Ultra High Performance Liquid Chromatography-mass analysis (UHPLC-MS): UPLC Waters Acquity, UV DAD, coupled to a mass spectrometer tandem quadrupole Waters Quattro Premier XE.

Column Acquity UPLC BEH C18 (2.1×50 mm) 1.7 μm, mobile phase: A $H_2O$+0.1% TFA, B: MeCN+0.1% TFA. Eluting conditions comprised a linear gradient (minute/% B): 0/5% B, 4/98% B, flow rate 0.4 ml/min.

1. Example 1: Preparation of 2-(4-chlorophenylamino)-4-(4-tert-butylaminopiperidin-1-yl)-quinoline hydrochloride Salt (1-6)

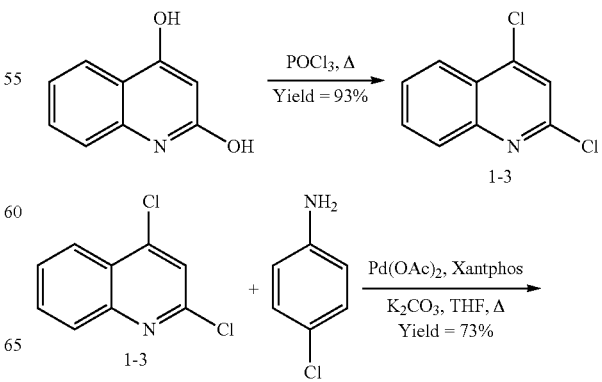

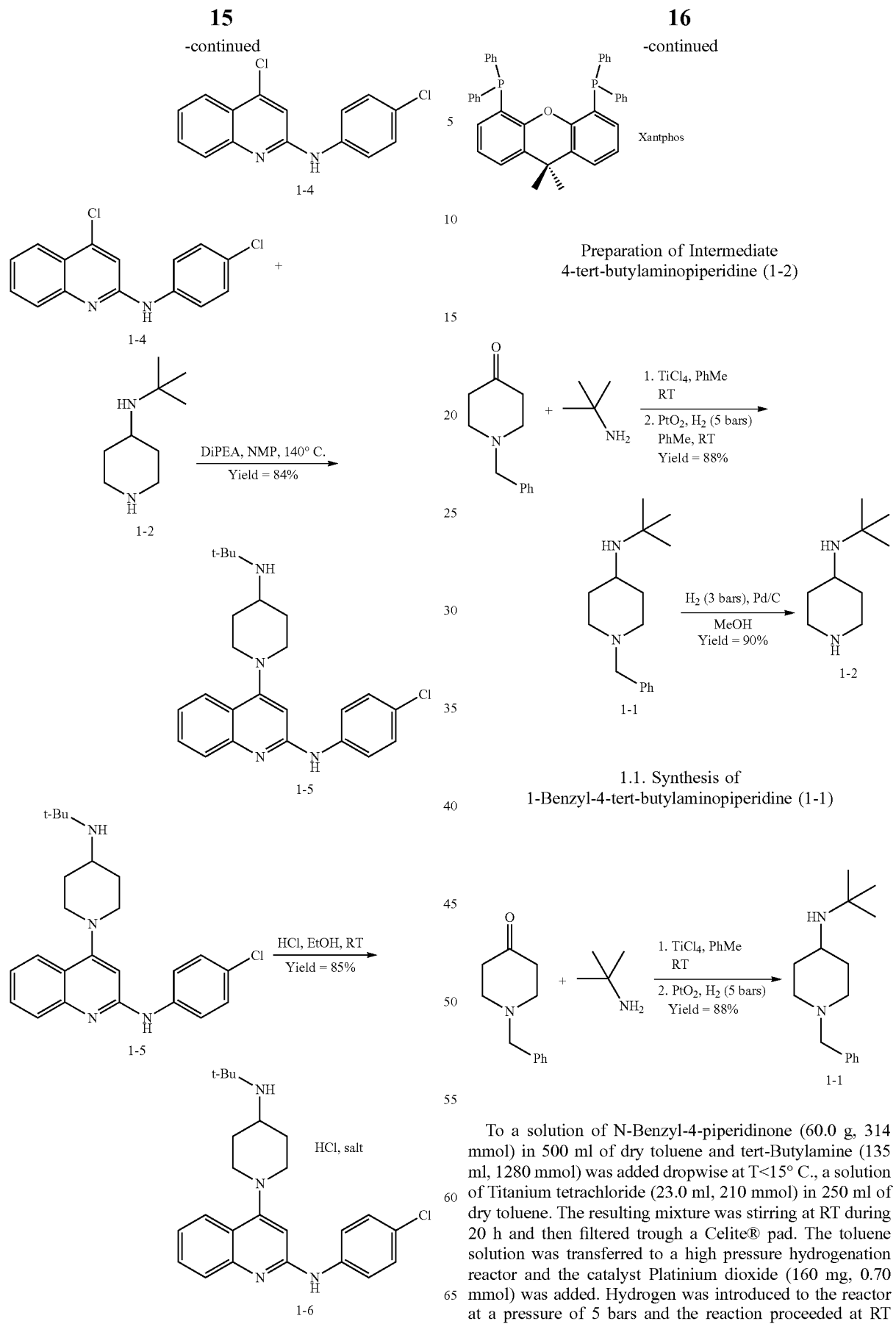

Preparation of Intermediate
4-tert-butylaminopiperidine (1-2)

1.1. Synthesis of
1-Benzyl-4-tert-butylaminopiperidine (1-1)

To a solution of N-Benzyl-4-piperidinone (60.0 g, 314 mmol) in 500 ml of dry toluene and tert-Butylamine (135 ml, 1280 mmol) was added dropwise at T<15° C., a solution of Titanium tetrachloride (23.0 ml, 210 mmol) in 250 ml of dry toluene. The resulting mixture was stirring at RT during 20 h and then filtered trough a Celite® pad. The toluene solution was transferred to a high pressure hydrogenation reactor and the catalyst Platinium dioxide (160 mg, 0.70 mmol) was added. Hydrogen was introduced to the reactor at a pressure of 5 bars and the reaction proceeded at RT during 2 days. Then, the resulting mixture was diluted with a 2 M NaOH aqueous solution (400 ml) and filtered through a Celite® pad. The layers were separated and the aqueous layer was extracted with toluene. The combined organic layers were dried over Na$_2$SO$_4$ filtered and concentrated under reduced pressure to give 68.05 g (yield 88%) of a orange oil corresponding to 1-Benzyl-4-tert-butylaminopiperidine.

Mass: (ES+) C$_{16}$H$_{26}$N$_2$ required 246; found 247 [M+H]
$^1$H NMR (300 MHz, CDCl$_3$)

1.2. Synthesis of 4-tert-butylaminopiperidine (1-2)

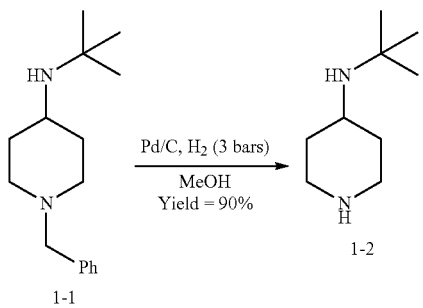 [SMILES: CC(C)(C)NC1CCN(Cc2ccccc2)CC1 ; CC(C)(C)NC1CCNCC1]

In a hydrogen chemical reactor and to a nitrogen degased solution of 1-Benzyl-4-tert-butylaminopiperidine (68.05 g, 276 mmol) in 700 ml of methanol was added under nitrogen Palladium on carbon powder 10 wt %, 50% wet (29.40 g, 13.81 mmol, 5 mol %). Hydrogen was introduced to the reactor at a pressure of 3 bars and the reaction proceeded at RT during 2 days. Then, the resulting mixture was filter through a Celite® pad and the filtrate was concentrated under reduced pressure to give 38.86 g (yield 90%) of a yellow solid corresponding to 4-tert-butylaminopiperidine.

Mass: (ES+) C$_9$H$_{20}$N$_2$ required 156; found 157 [M+H]
$^1$H NMR (300 MHz, CDCl$_3$)

1.3. Synthesis of 2,4-dichloroquinoline (1-3)

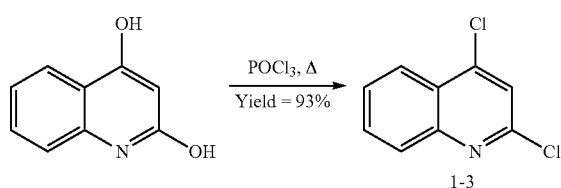 [SMILES: Oc1cc(O)c2ccccc2n1 ; Clc1cc(Cl)c2ccccc2n1]

To quinoline-2,4-diol (50.0 g, 310 mmol) was added dropwise at 0° C. Phosphoryl chloride (250 ml, 2682 mmol). The resulting mixture was stirred and heated under reflux overnight. Then, the mixture was cooled, concentrated under reduced pressure and coevapored twice times with 500 ml of toluene. The residue was then taken up with DCM (500 ml) and washed with cold water. The aqueous layer was extracted with DCM and the combined organic layers were combined and dried over MgSO$_4$, filtered and concentrated under reduced pressure to give a brown solid (57.0 g, yield 93%) corresponding to 2,4-dichloroquinoline.

Mass: (ES+) C$_9$H$_5$Cl$_2$N required 197; found 198 [M+H]
$^1$H NMR (300 MHz, CDCl$_3$)

1.4. Synthesis of 2-(4-chlorophenylamino)-4-chloroquinoline (1-4)

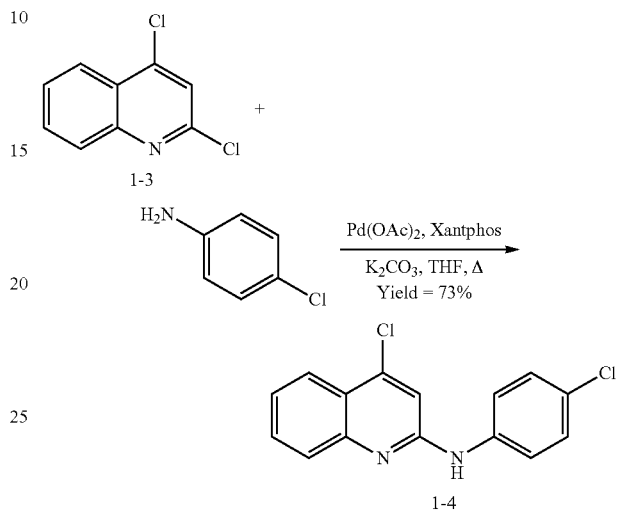

To a solution, under nitrogen gas, of 2,4-dichloroquinoline (2.00 g, 10.1 mmol) in dry THF (20 ml) was added 4-chloroaniline (1.45 g, 11.1 mmol) and K$_2$CO$_3$ (3.91 g, 28.3 mmol). The resulting mixture was degassed 5 min with nitrogen, then Xantphos (590 mg, 1.01 mmol) and Pd(OAc)$_2$ (120 mg, 0.5 mmol) were added and the reaction mixture was heated under reflux for 2 h. The reaction mixture was then cooled to RT and concentrated under reduced pressure. The residue was partitioned between water and AcOEt and the aqueous layer was extracted with AcOEt. The combined organic layers were dried over Na$_2$SO$_4$, filtered and concentrated under reduced pressure to give a yellow oil. The crude product was purified by flash chromatography (gradient cyclohexane/AcOEt from 7/3 to 0/10) to give 2.13 g (yield 73%) of a yellow solid corresponding to 2-(4-chlorophenylamino)-4-chloroquinoline.

Mass: (ES+) C$_{15}$H$_{10}$Cl$_2$N$_2$ required 288; found 289 [M+H]
$^1$H NMR (300 MHz, CDCl$_3$)

1.5. Synthesis of 2-(4-chlorophenylamino)-4-(4-tert-butylaminopiperidin-1-yl)-quinoline (1-5)

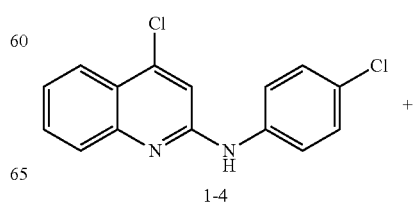

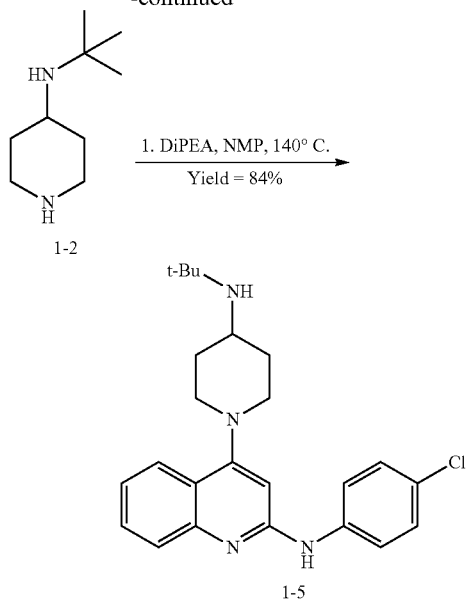

To a solution of 2-(4-chlorophenylamino)-4-chloroquinoline (1.00 g, 3.46 mmol) and 4-(tert-butylamino)-piperidine (684 mg, 4.38 mmol) in 5 ml of NMP was added N,N-Diisopropylethylamine (0.947 ml, 5.47 mmol) and the mixture was heated for 24 h at 140° C. Then, the reaction mixture was cooled, diluted with a 1N NaOH aqueous solution and the resulting mixture was extracted with AcOEt. The combined organic layers were dried over Na$_2$SO$_4$, filtered and concentrated under reduced pressure to give a brown liquid. The crude product was purified by flash chromatography (gradient cyclohexane/AcOEt from 8/2 to 2/8) to give a yellowish solid. This solid was recrystallized from MeCN to give 1.19 g (yield 84%) of a white solid corresponding to 2-(4-chlorophenylamino)-4-(4-tert-butylaminopiperidin-1-yl)-quinoline.

HPLC-MS: t$_r$=1.24 min, (ES+) C$_{24}$H$_{29}$ClN$_4$ required 408; found 409 [M+H], 353 [M-tBu+H]

$^1$H NMR (300 MHz, CDCl$_3$)

1.6. Synthesis of 2-(4-chlorophenylamino)-4-(4-tert-butylaminopiperidin-1-yl)-quinoline hydrochloride Salt (1-6)

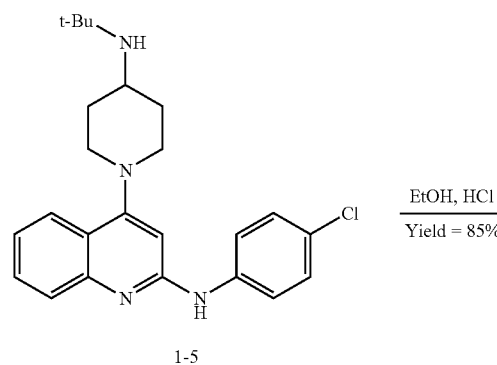

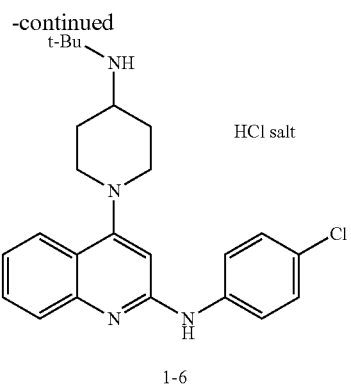

To a suspension of 2-(4-chlorophenylamino)-4-(4-tert-butylaminopiperidin-1-yl)-quinoline (440 mg, 1.1 mmol) in 4 ml of EtOH was added dropwise 371 μL of a 7.25 M solution of HCl in EtOH. The solid dissolved and the mixture was stirred 20 min at RT. Then, the resulting solution was concentrated to about the half volume under reduced pressure and 6 ml of ether were added. The resulting mixture was stirred 1 h at room temperature to obtain a white solid which was filtered off, rinsed with ether and dried under vacuum at 45° C. to give 401 mg (yield 85%) of a white solid corresponding to 2-(4-chlorophenylamino)-4-(4-tert-butylaminopiperidin-1-yl)-quinoline hydrochloride salt.

HPLC-MS: t$_r$=1.21 min, (ES+) C$_{24}$H$_{29}$ClN$_4$ required 408; found 409 [M+H], 353 [M-tBu+H]

$^1$H NMR (300 MHz, CD$_3$OD)

$^{13}$C NMR (75 MHz, CD$_3$OD)

2. Example 2: Preparation of 2-(4-chlorobenzylamino)-4-(4-tert-butylaminopiperidin-1-yl)-quinoline hydrochloride Salt (2-3)

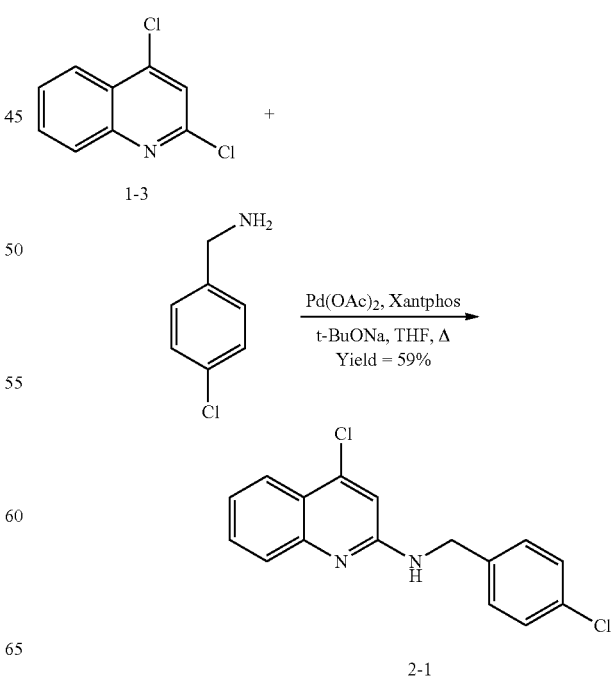

-continued 2-1 + 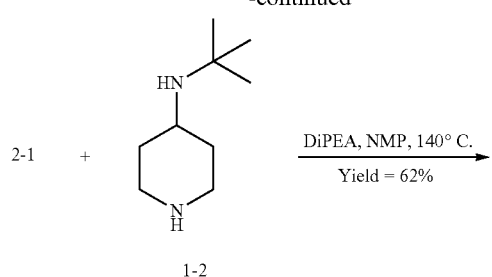

1-2

DiPEA, NMP, 140° C.
Yield = 62%

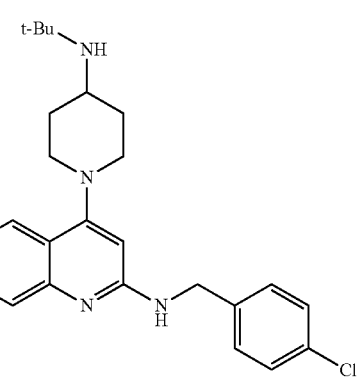

2-2

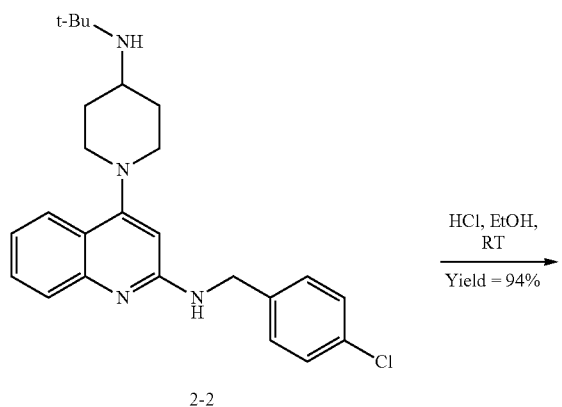

2-2

HCl, EtOH, RT
Yield = 94%

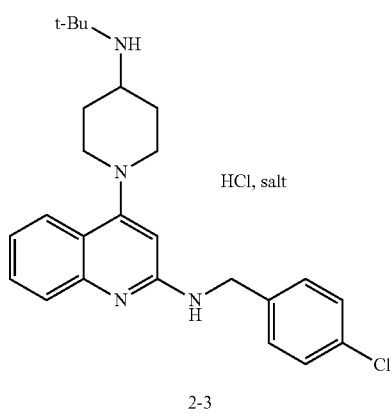 [SMILES: CC(C)(C)NC1CCN(c2cc(NCc3ccc(Cl)cc3)nc3ccccc23)CC1]

2-3

HCl, salt

2.1. Synthesis of 2-(4-chlorobenzylamino)-4-chloroquinoline (2-1)

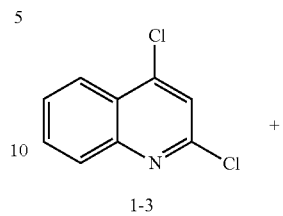

1-3

+

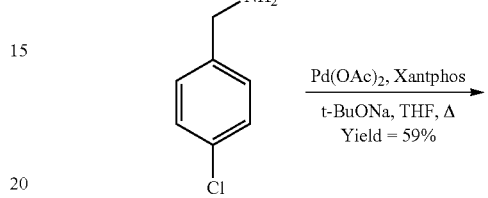

Pd(OAc)$_2$, Xantphos
t-BuONa, THF, Δ
Yield = 59%

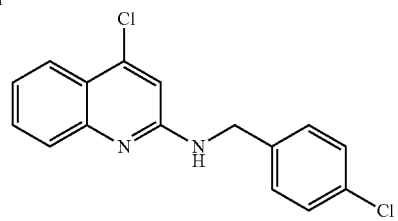

2-1

To a solution under nitrogen gas of 2,4-dichloroquinoline (1.00 g, 5.05 mmol) in dry THF (10 ml) was added 4-chlorobenzylamine (1.46 g, 10.1 mmol) and t-BuONa (1.36 g, 14.1 mmol). The resulting mixture was degassed 5 min with nitrogen, then Xantphos (295 mg, 0.51 mmol) and Pd(OAc)$_2$ (58 mg, 0.25 mmol) were added and the reaction mixture was heated under reflux for 2 h. The reaction mixture was then cooled to RT and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude product was purified by flash chromatography (gradient cyclohexane/DCM from 5/5 to 0/10) to give 897 mg (yield 59%) of a brown solid corresponding to 2-(4-chlorobenzylamino)-4-chloroquinoline.

Mass: (ES+) C$_{16}$H$_{12}$Cl$_2$N$_2$ required 302; found 303 [M+H]

$^1$H NMR (300 MHz, CDCl$_3$)

2.2. Synthesis of 2-(4-chlorobenzylamino)-4-(4-tert-butylaminopiperidin-1-yl)-quinoline (2-2)

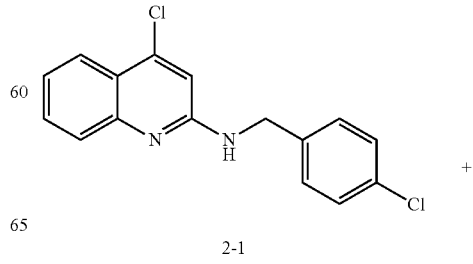

2-1

+

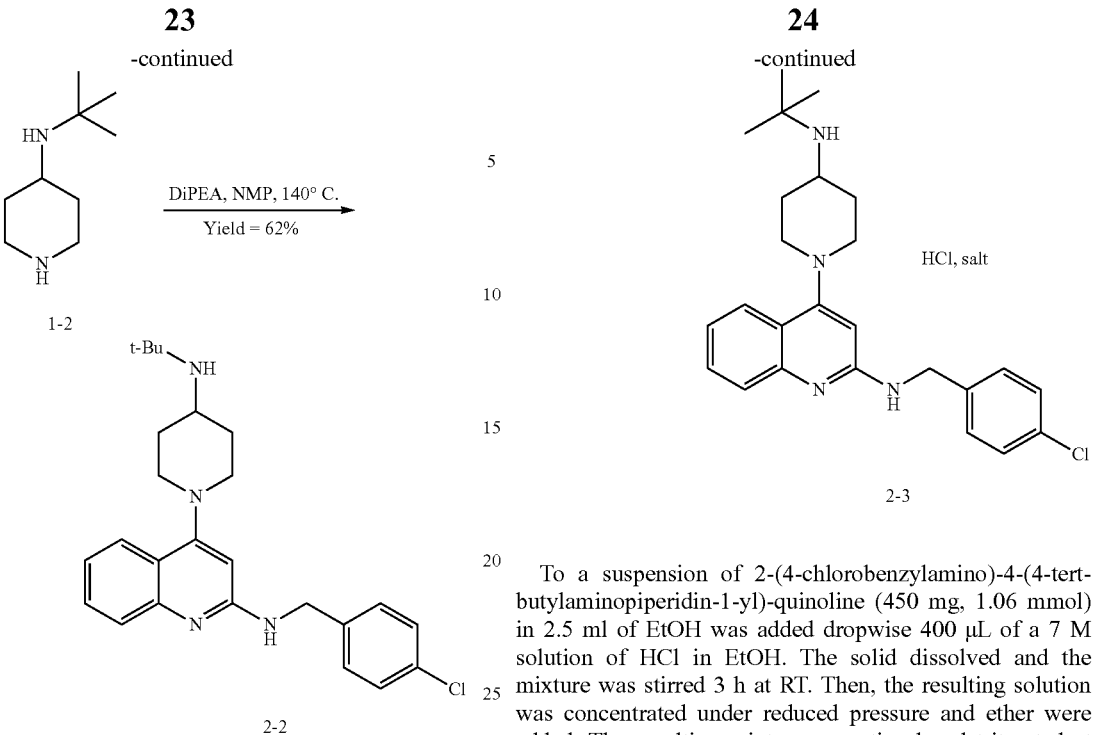

To a solution of 2-(4-chlorobenzylamino)-4-chloroquinoline (1.05 g, 3.46 mmol) and 4-(tert-butylamino)-piperidine (0.684 g, 4.38 mmol) in 5 ml of NMP was added N,N-Diisopropylethylamine (0.947 ml, 5.47 mmol) and the mixture was heated for 22 h at 140° C. Then, the reaction mixture was cooled, diluted with a 1N NaOH aqueous solution and the resulting mixture was extracted with AcOEt. The combined organic layers were dried over $Na_2SO_4$, filtered and concentrated under reduced pressure to give a yellow oil. The crude product was purified by flash chromatography (gradient cyclohexane/AcOEt from 8/2 to 0/10) to give a yellow solid. This solid was recrystallized from MeCN to give 904 mg (yield 62%) of a white solid corresponding to 2-(4-chlorobenzylamino)-4-(4-tert-butylaminopiperidin-1-yl)-quinoline.

HPLC-MS: $t_r$=1.30 min, (ES+) $C_{25}H_{31}ClN_4$ required 422; found 423 [M+H], 368 [M-tBu+H]

$^1$H NMR (300 MHz, $CDCl_3$)

2.3. Synthesis of 2-(4-chlorobenzylamino)-4-(4-tert-butylaminopiperidin-1-yl)-quinoline hydrochloride Salt (2-3)

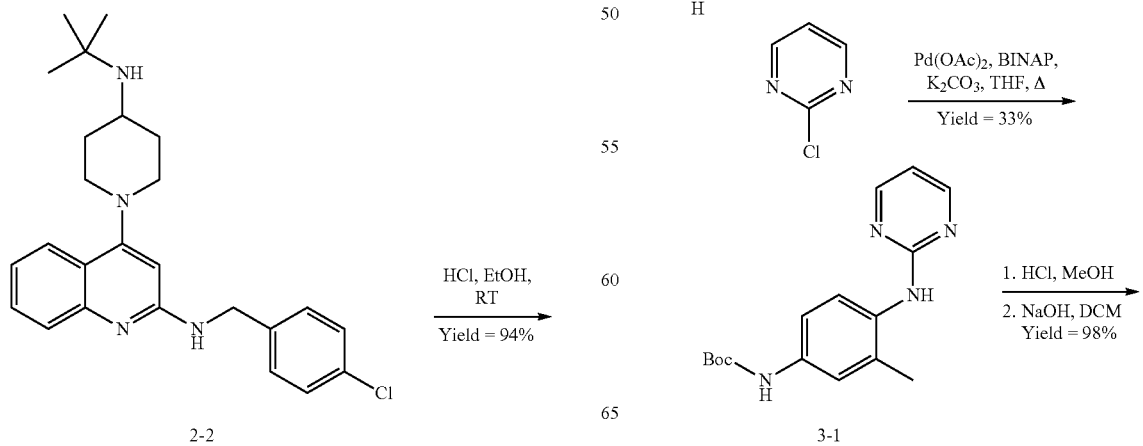

To a suspension of 2-(4-chlorobenzylamino)-4-(4-tert-butylaminopiperidin-1-yl)-quinoline (450 mg, 1.06 mmol) in 2.5 ml of EtOH was added dropwise 400 μL of a 7 M solution of HCl in EtOH. The solid dissolved and the mixture was stirred 3 h at RT. Then, the resulting solution was concentrated under reduced pressure and ether were added. The resulting mixture was stirred and triturated at room temperature to obtain a yellowish solid which was filtered off, rinsed with ether and dried under vacuum. The yellowish solid was dissolved in pure water and was then freeze-dried to give 401 mg (yield 94%) of a white solid corresponding to 2-(4-chlorobenzylamino)-4-(4-tert-butylaminopiperidin-1-yl)-quinoline hydrochloride salt.

HPLC-MS: $t_r$=1.31 min, (ES+) $C_{25}H_{31}ClN_4$ required 422; found 423 [M+H], 369 [M-tBu+H]

$^1$H NMR (300 MHz, DMSO-$d_6$)

3. Example 3: Preparation of 2-[3-methyl-4-(pyrimidin-2-ylamino)phenylamino]-4-(4-tert-butylaminopiperidin-1-yl)-quinoline hydrochloride Salt (3-5)

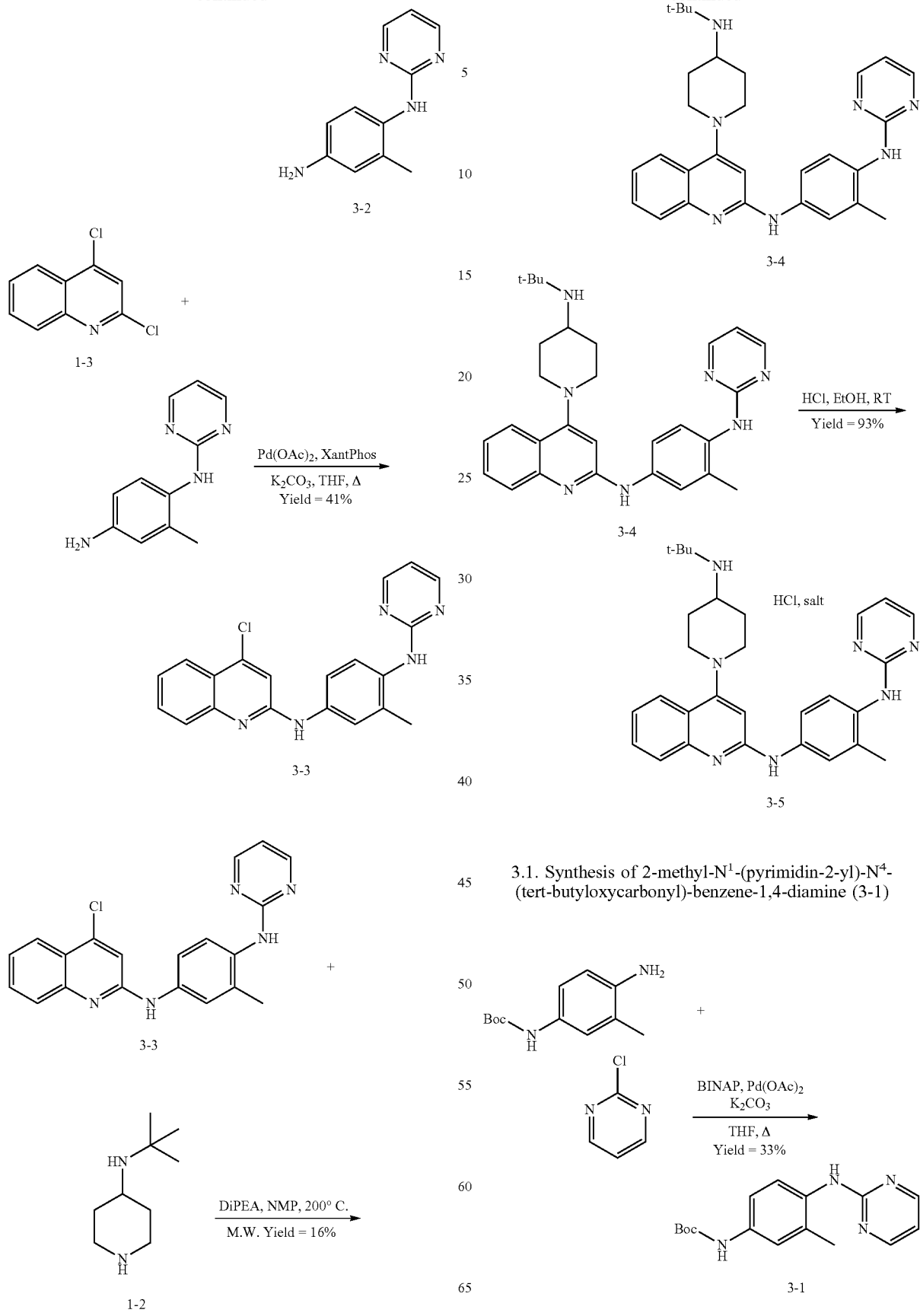
3.1. Synthesis of 2-methyl-$N^1$-(pyrimidin-2-yl)-$N^4$-(tert-butyloxycarbonyl)-benzene-1,4-diamine (3-1)

A solution of 2-methyl-N⁴-(tert-butyloxycarbonyl)-benzene-1,4-diamine (2.40 g, 10.8 mmol), 2-chloropyrimidine (0.78 g, 6.5 mmol) and K₂CO₃ (2.24 g, 16.2 mmol) in dry THF (48 ml) was degassed with nitrogen during 15 minutes. Then, Pd(OAc)₂ (58 mg, 0.26 mmol) and BINAP ligand (320 mg, 0.52 mmol) was added and the reaction mixture was degassed a second time during 20 minutes. The reaction mixture was finally heated under reflux for 1 h. The reaction mixture was then cooled to RT and concentrated under reduced pressure. The residue was partitioned between water and AcOEt and the aqueous layer was extracted with AcOEt. The combined organic layers were dried over Na₂SO₄, filtered and concentrated under reduced pressure. The crude product was purified by flash chromatography (gradient cyclohexane/AcOEt from 10/0 to 7/3) to give 650 mg (yield 33%) of a brown solid corresponding to 2-methyl-N¹-(pyrimidin-2-yl)-N⁴-(tert-butyloxycarbonyl)-benzene-1,4-diamine.

HPLC-MS: t$_r$=2.06 min, (ES+) C₁₆H₂₀N₄O₂ required 300; found 301 [M+H]

¹H NMR (300 MHz, CD₃OD)

3.2. Synthesis of 2-methyl-N1-(pyrimidin-2-yl)-benzene-1,4-diamine (3-2)

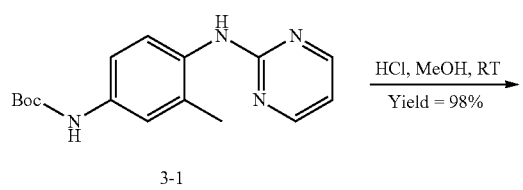

To 2-methyl-N¹-(pyrimidin-2-yl)-N4-(tert-butyloxycarbonyl)-benzene-1,4-diamine (1.18 g, 3.93 mmol) was added dropwise at RT a 3M HCl solution in methanol (15 ml). Then, the reaction mixture was stirred during 1 h at RT. The reaction was then concentrated under reduced pressure and the residue was partition between DCM and a 1M NaOH aqueous solution and the aqueous layer was extracted with DCM. The combined organic layers were dried over Na₂SO₄, filtered and concentrated under reduced pressure to give 787 mg (yield 98%) of a yellow oil corresponding to 2-methyl-N1-(pyrimidin-2-yl)benzene-1,4-diamine.

Mass: (ES+) C₁₁H₁₂N₄ required 200; found 201 [M+H]

¹H NMR (300 MHz, CD₃OD)

3.3. Synthesis of 2-[4-(2-pyrimidinylamino)-3-methyl-phenylamino]-4-chloroquinoline (3-3)

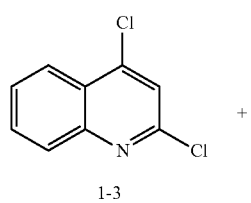

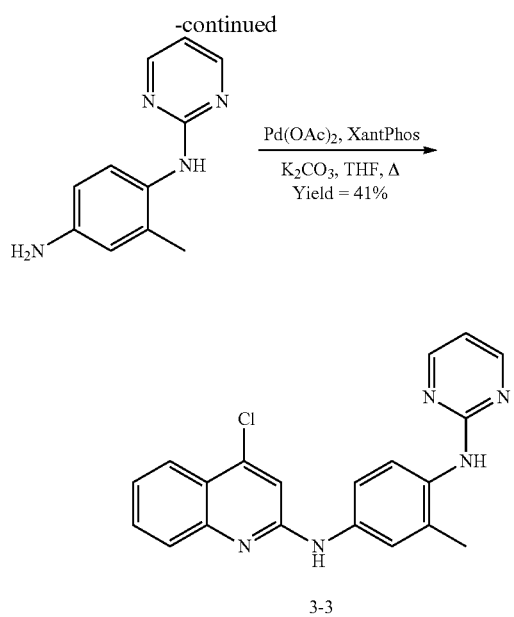

A solution of 2-methyl-N¹-(pyrimidin-2-yl)benzene-1,4-diamine (771 mg, 3.85 mmol), 2,4-dichloroquinoline (693 mg, 3.5 mmol) and K₂CO₃ (1.35 g, 9.80 mmol) in dry THF (7 ml) was degassed with nitrogen during 20 minutes. Then, Pd(OAc)₂ (47 mg, 0.21 mmol) and XantPhos ligand (61 mg, 0.10 mmol) was added and the reaction mixture was degassed a second time during 20 minutes. The reaction mixture was finally heated under reflux for 4 h. The reaction mixture was then cooled to RT and concentrated under reduced pressure. The residue was partitioned between water and AcOEt and the aqueous layer was extracted with AcOEt. The combined organic layers were dried over Na₂SO₄, filtered and concentrated under reduced pressure. The crude product was purified by flash chromatography (gradient cyclohexane/AcOEt from 10/0 to 5/5) to give 520 mg (yield 41%) of a yellow solid corresponding to 2-[4-(2-pyrimidinylamino)-3-methyl-phenylamino]-4-chloroquinoline.

Mass: (ES+) C₂₀H₁₆ClN₅ required 361; found 362 [M+H]

3.4. Synthesis of 2-[4-(2-pyrimidinylamino)-3-methyl-phenylamino]-4-(4-tert-butylaminopiperidin-1-yl)-quinoline (3-4)

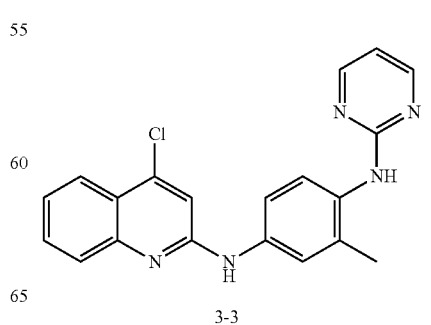

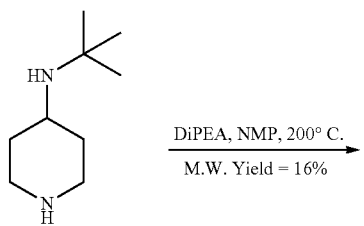

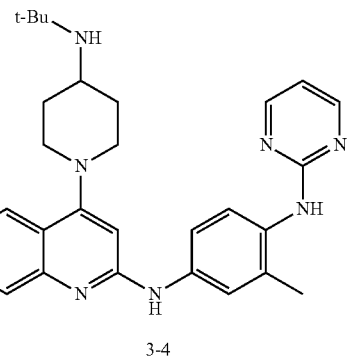

To a solution of 2-[4-(2-pyrimidinylamino)-3-methyl-phenylamino]-4-chloroquinoline (350 mg, 0.97 mmol) in NMP (1.5 ml) was added 4-tert-butylaminopiperidine (760 mg, 4.80 mmol). The resulting solution was heated for 30 minutes at 200° C. in a laboratory microwave oven. Then, the resulting mixture was cooled and partitioned between water and AcOEt and the aqueous layer was extracted with AcOEt. The combined organic layers were dried over $Na_2SO_4$, filtered and concentrated under reduced pressure. The crude product was purified by flash chromatography (gradient cyclohexane/AcOEt from 10/0 to 5/5) to give 75 mg (yield 16%) of a brown solid corresponding to 2-[4-(2-pyrimidinylamino)-3-methyl-phenylamino]-4-(4-tert-butylaminopiperidin-1-yl)-quinoline.

HPLC-MS: $t_r$=1.15 min, (ES+) $C_{29}H_{35}N_7$ required 481; found 482 [M+H], 426 [M-tBu+H]

3.5. Synthesis of 2-[4-(2-pyrimidinylamino)-3-methyl-phenylamino]-4-(4-tert-butylaminopiperidin-1-yl)-quinoline hydrochloride Salt (3-5)

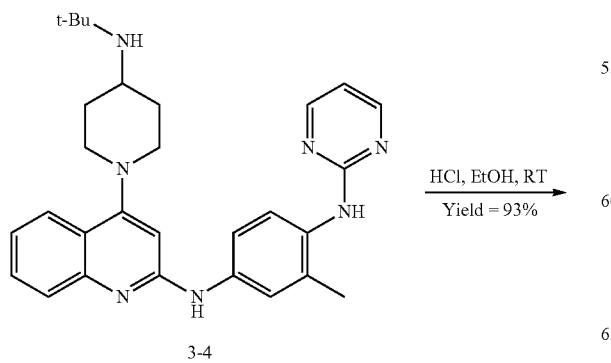

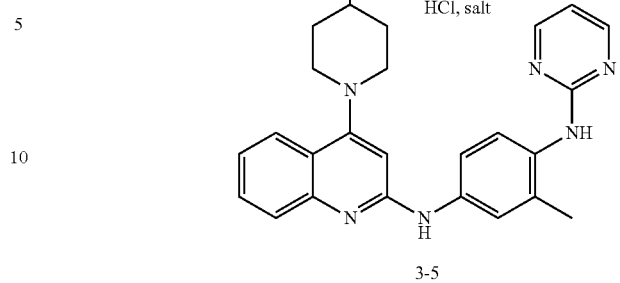

A 3.0 M solution of HCl in EtOH (290 µL) was added dropwise to 2-[4-(2-pyrimidinylamino)-3-methyl-phenylamino]-4-(4-tert-butylaminopiperidin-1-yl)-quinoline (75 mg, 0.16 mmol). The resulting mixture was filtered and evaporated under reduced pressure to give 80 mg (yield 93%) of a yellowish solid corresponding to 2-[4-(2-pyrimidinylamino)-3-methyl-phenylamino]-4-(4-tert-butylaminopiperidin-1-yl)-quinoline hydrochloride salt.

HPLC-MS: $t_r$=1.15 min, (ES+) $C_{29}H_{35}N_7$ required 481; found 482 [M+H], 426 [M-tBu+H]

$^1$H NMR (300 MHz, $CD_3OD$+few drops of DMSO-$d_6$)

4. Example 4: Preparation of 2-[3-methyl-4-(pyrimidin-2-ylamino)phenylamino]-4-(4-tert-butylaminopiperidin-1-yl)-quinoline hydrochloride Salt (4-3)

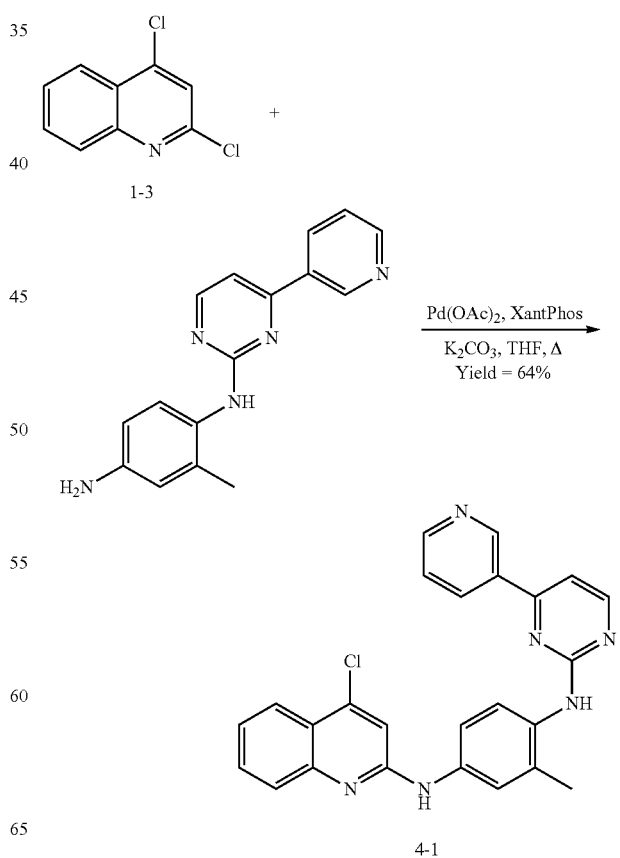

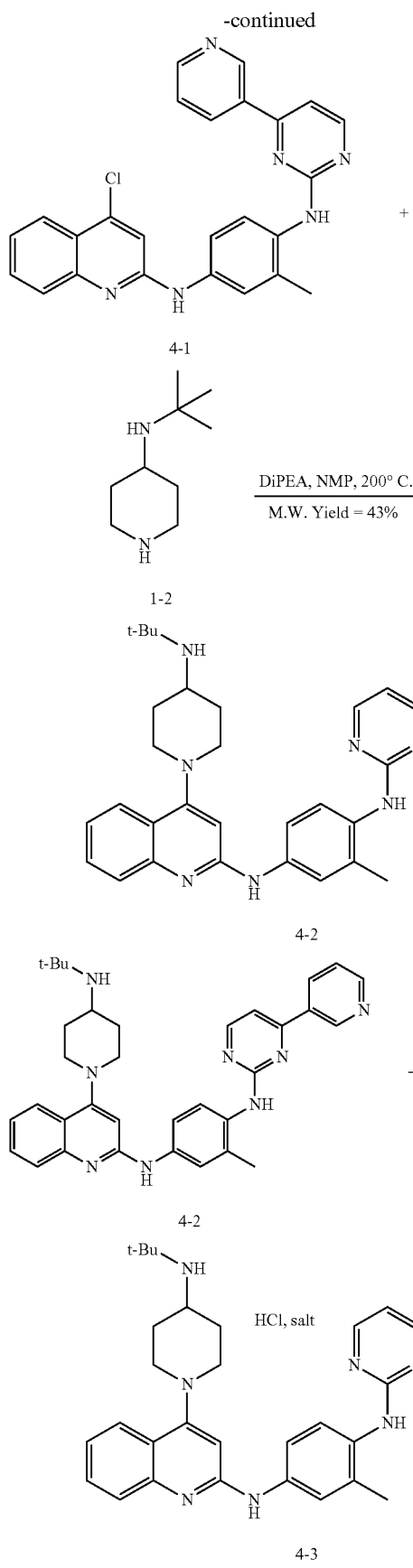

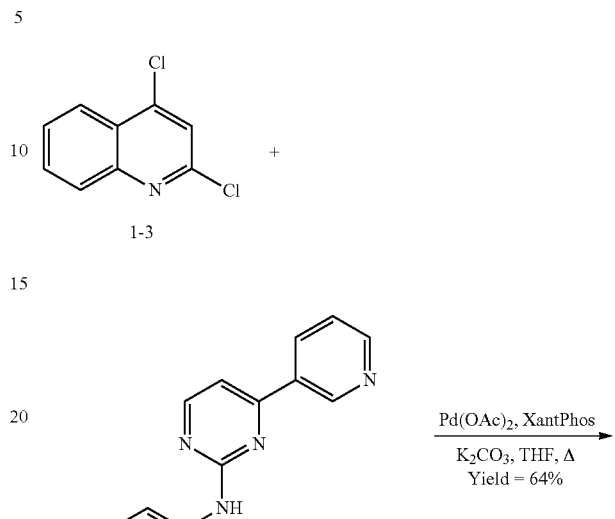

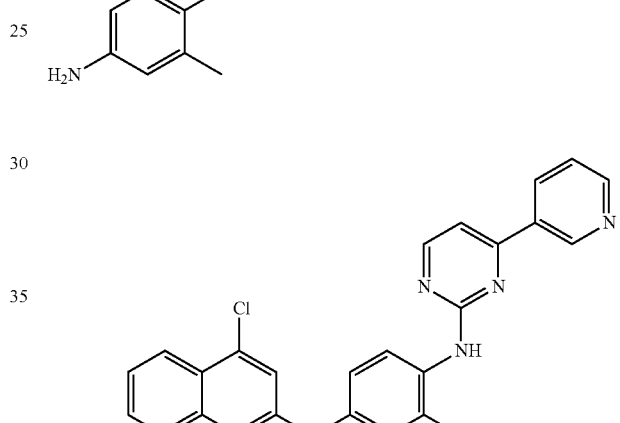

4.1. Synthesis of 2-{4-[4-(pyridine-3-yl)-2-pyrimidinamino]-3-methyl-phenylamino}-4-chloroquinoline (4-1)

A solution of 2-methyl-N¹-[4-(pyridine-3-yl)-pyrimidin-2-yl]benzene-1,4-diamine (1.18 g, 4.26 mmol), 2,4-dichloroquinoline (767 mg, 3.87 mmol) in dry THF (11.9 ml) was added K₂CO₃ (2.7 g, 19.0 mmol) and the reaction mixture was degassed with nitrogen during 15 minutes. Then, XantPhos ligand (226 mg, 0.387 mmol) and Pd(OAc)₂ (44 mg, 0.19 mmol) was added and the reaction mixture was degassed a second time during 15 minutes. The reaction mixture was finally heated under reflux overnight. The reaction mixture was then cooled to RT and concentrated under reduced pressure. The residue was partitioned between water and AcOEt and the aqueous layer was extracted with AcOEt. The combined organic layers were dried over Na₂SO₄, filtered and concentrated under reduced pressure. The crude product was purified by flash chromatography (gradient cyclohexane/AcOEt from 10/0 to 0/10) to give 1.08 g (yield 64%) of a brown solid corresponding to 2-{4-[4-(pyridin-3-yl)-2-pyrimidinamino]-3-methyl-phenylamino}-4-chloroquinoline.

Mass: (ES+) $C_{25}H_{19}ClN_6$ required 438; found 439 [M+H]
¹H NMR (300 MHz, CD₃OD)

4.2. Synthesis of 2-{4-[4-(pyridin-3-yl)-2-pyrimidinamino]-3-methyl-phenylamino}-4-(4-tert-butylaminopiperidin-1-yl)-quinoline (4-2)

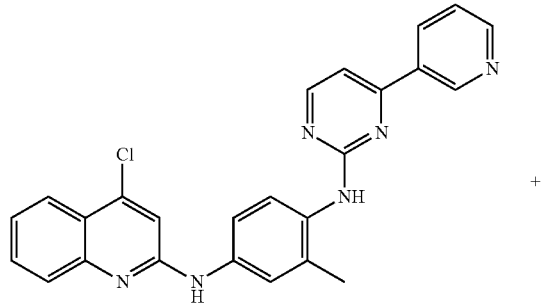

4-1

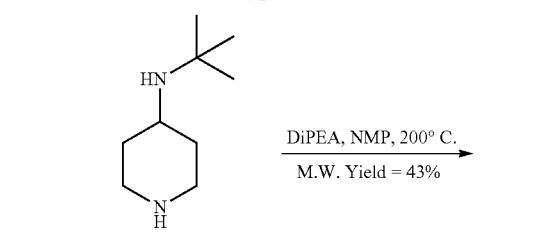

1-2

DiPEA, NMP, 200° C.
M.W. Yield = 43%

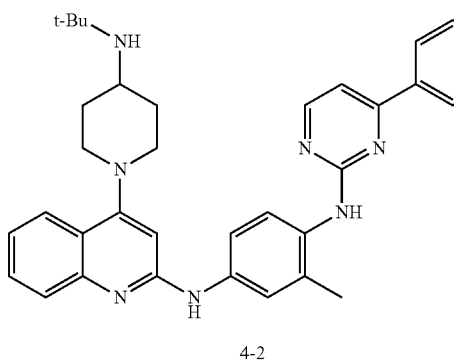

4-2

To a solution of 2-{4-[4-(pyridin-3-yl)-2-pyrimidinamino]-3-methyl-phenylamino}-4-chloroquinoline (1.0 g, 2.28 mmol) in NMP (10 ml) was added 4-tert-butylaminopiperidine (1.8 g, 11.0 mmol). The resulting solution was heated for 90 minutes at 200° C. in a laboratory microwave oven. The resulting mixture was partitioned between water and AcOEt and the aqueous layer was extracted with AcOEt. The combined organic layers were dried over $Na_2SO_4$, filtered and concentrated under reduced pressure. The crude product was purified by flash chromatography (from AcOEt/DCM 3/2 then DCM/MeOH 9/1) to give 1.01 g of a yellow solid which was recrystallized from EtOH to give 550 mg (yield 43%) of a white solid corresponding to 2-{4-[4-(pyridin-3-yl)-2-pyrimidinamino]-3-methyl-phenylamino}-4-(4-tert-butylaminopiperidin-1-yl)-quinoline.

HPLC-MS: $t_r$=1.20 min, (ES+) $C_{34}H_{38}N_8$ required 558; found 559 [M+H], 503 [M-tBu+H]

$^1$H NMR (300 MHz, DMSO-$d_6$)

4.3. Synthesis of 2-{4-[4-(pyridin-3-yl)-2-pyrimidinamino]-3-methy-phenylamino}-4-(4-tert-butylaminopiperidin-1-yl)-quinoline hydrochloride salt (4-3)

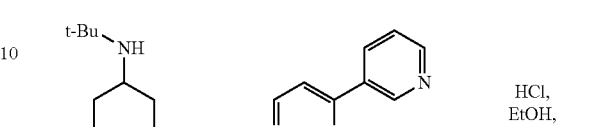

4-2

HCl, EtOH, RT
Yield = 77%

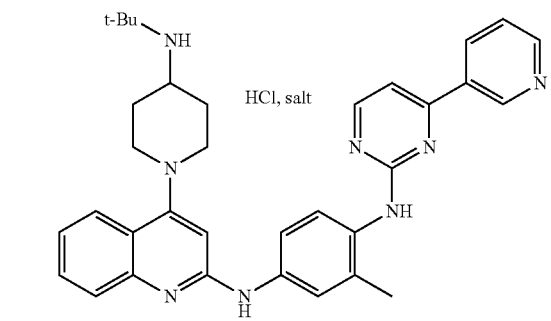

4-3

To a suspension of 2-{4-[4-(pyridin-3-yl)-2-pyrimidinamino]-3-methyl-phenylamino}-4-(4-tert-butylaminopiperidin-1-yl)-quinoline in EtOH (5.5 ml) was added dropwise a 3.0 M solution of HCl in EtOH (4 ml). The formed yellow solid was filtered off and then triturated with cyclohexane. The suspension was filtered off to give 505 mg (yield 77%) of a white solid corresponding to 2-{4-[4-(pyridin-3-yl)-2-pyrimidinamino]-3-methyl-phenylamino}-4-(4-tert-butylaminopiperidin-1-yl)-quinoline hydrochloride salt.

HPLC-MS: $t_r$=1.22 min, (ES+) $C_{34}H_{38}N_8$ required 558; found 559 [M+H], 503 [M-tBu+H]

$^1$H NMR (300 MHz, CD$_3$OD+few drops of DMSO-$d_6$)
$^{13}$C NMR (125 MHz, CD$_3$OD)

5. Example 5: Activity Profile of Compounds 1-6, 2-3, 3-5 and 4-3 in MOLM-14, KG-1, MV4-11, A375, HCT-116, HepG2, Huh-7, MRC-5, MDA-MB-231, ARPE-19 Cell Lines and PBMC Cells Cell Culture:

All cell lines were maintained in medium containing 1% penicillin-streptomycin (Dutscher, P06-07100) and 10% Fetal Bovine Serum (Gibco, W3387L) except 20% for KG-1 cell line and PBMC, and cultured at 37° C. with 5% $CO_2$.

HepG2, Huh7, HCT-116, MDA-MB-231 and A375 cell lines were cultured in Dulbecco's modified Eagle's medium (Dutscher, L0103).

KG-1 and MV4-11 cell line were maintained in Iscove's modified Dulbecco's medium (Dutscher, L0190).

MOLM-14 cell line was maintained in MEM alpha medium (Gibco, 22561-021).

PBMC was maintained in RPMI 1640 medium medium (Dutscher, L0498).

MRC-5 cell line was maintained in MEM (Dutscher, L0416).

ARPE-19 cell line was cultured in DMEM:F12 medium (Dutscher, L0093).

Cell Viability Assay:

Cell viability was measured using the CellTiter-Glo® luminescent cell viability assay as described by the manufacturer (Promega, Ref G7571) using an Infinite F200Pro luminometer (Tecan). Briefly, for adherent cells, cells were plated onto 96-well plates (white with clear bottom) in 90 μL of media per well and were allowed to grow overnight before the assay. For cells growing in suspension, cells were plated onto 96-well plates immediately before the assay. The number of cells seeded per well is indicated in the table 1 below:

TABLE 1

Number of cells seeded per well for cell viability assays

| Entry | Cell lines | Cell number per well |
|---|---|---|
| 1 | HCT-116 | 2,000 |
| 2 | A375 | 800 |
| 3 | Huh7 | 10,000 |
| 4 | HepG2 | 7,500 |
| 5 | MOLM-14 | 10,000 |
| 6 | KG-1 | 20,000 |
| 7 | MV4-11 | 20,000 |
| 8 | PBMC | 10,000 |
| 9 | MRC-5 | 5,000 |
| 10 | ARPE-19 | 5,000 |
| 11 | MDA-MB-231 | 10,000 |

Compounds were added at different concentrations to each well, and cell cultures were incubated for 72 h. Vehicle ($H_2O$) was used as a control, and all compounds were tested in a constant percentage of $H_2O$. After addition of 100 μL of CellTiter-Glo®, luminescence was measured using an Infinite F200Pro (Tecan). $EC_{50}$ values were determined as the dose of compound required to reduce luminescent values to 50% of the signal obtained for untreated cell cultures. The experimental data were analyzed using a computer program, Graphpad Prism v5 (GraphPad Software, Inc. La Jolla, Calif.).

All experiments were at least done in duplicate and repeated two independent times.

TABLE 2

Growth inhibition assay of MOLM-14 cell line in presence of compound 1-6, 2-3, 3-5, 4-3

| Compounds | % Cell viability of MOLM-14 cell line | |
|---|---|---|
| Concentrations | 10 μM | 4 μM |
| 1-6 | 12.1 | 71.8 |
| 2-3 | 0.3 | 31.8 |
| 3-5 | 8.7 | 78.7 |
| 4-3 | 0.2 | 0.5 |

TABLE 3

Growth inhibition assay of MOLM-14, KG-1, MV4-11 cell lines and PBMC in presence of compound 2-3

| Cells | MOLM-14 | KG-1 | MV4-11 | PBMC |
|---|---|---|---|---|
| Description | Acute myeloid leukemia | Acute myelogenous leukemia | biphenotypic B myelomonocytic leukemia | Peripheral blood mononuclear cell |
| | FLT3-ITD Heterozygote+/− | FLT3-ITD WT−/− FGFR1 fusions | FLT3-ITD Homozygote+/+ | |
| $EC_{50}$ (μM) | 2.2 | 5.1 | 2.3 | 1.9 |

TABLE 4

Growth inhibition assay of A375, HCT-116, HepG2 and Huh-7 cell lines in presence of compound 2-3

| Cell lines | A375 | HCT-116 | HepG2 | Huh-7 |
|---|---|---|---|---|
| Description | Malignant melanoma | Colorectal carcinoma | Hepatocellular carcinoma | Hepatocellular carcinoma |
| $EC_{50}$ (μM) | 1.0 | 1.6 | 0.9 | 1.7 |

TABLE 5

Growth inhibition assay of MRC-5, MDA-MB-231 and ARPE-19 cell lines in presence of compound 2-3

| Cell lines | MRC-5 | MDA-MB-231 | ARPE-19 |
|---|---|---|---|
| Description | Human fetal lung fibroblast | Breast adenocarcinoma | Human retinal pigmented epithelium |
| $EC_{50}$ (μM) | ≈3.4 | 2.0 | ≈6.9 |

TABLE 6

Growth inhibition assay of MOLM-14, A375, HCT-116 and HepG2 cell lines in presence of compound 4-3

| Cell lines | MOLM-14 | A375 | HCT-116 | HepG2 |
|---|---|---|---|---|
| Description | Acute myeloid leukemia | Malignant melanoma | Colorectal carcinoma | Hepatocellular carcinoma |
| $EC_{50}$ (μM) | 2.3 | 1.4 | 1.8 | 6.3 |

6. Example 6: ALDH+ Compartment Analysis in MOLM-14 Cell Line

MOLM-14 cell line was cultured in MEM alpha medium supplemented with 10% v/v Fetal Bovine Serum, 1% Penicillin-Streptomycin and maintained at 37° C. with 5% $CO_2$. 10,000 cells were plated onto 96-well plates immediately before the assay.

Each compound was added at different concentrations (combinations of six concentrations) to each well, and cell cultures were incubated for 72 h. Vehicle ($H_2O$) was used as a control, and all compounds were tested in a constant percentage of vehicle. Cell outgrowth was measured using the CellTiter-Glo® luminescent cell viability assay as described by the manufacturer (Promega, Ref G7571 Madison, Wis., USA) using a Centro (Berthold, France) plate reader.

In each experiment, each point represents the average of triplicates in cell culture.

The experimental data are analyzed using a computer program, Graphpad Prism v5 (GraphPad Software, Inc. La Jolla, Calif.) and $EC_{50}$ values were determined as the dose of compound required to reduce absorbance values to 50% of the signal obtained for vehicle treated cell cultures.

Analysis of the of aldehyde dehydrogenase (ALDH) compartment and high activity level of aldehyde dehydrogenase activity (ALDH+) was used to detect tumor initiating cells (cancer stem cells, CSC) population. The Aldefluor™ kit assay (StemCell Technologies, 01700) allowed to assess the activity of drugs on CSC cells like in a MOLM-14 acute myeloid leukemia cell line population (ref: Storms, R. W., Trujillo, A. P., Springer, J. B., Shah, L., Colvin, O. M., Ludeman, S. M., & Smith, C. (1999). Isolation of primitive human hematopoietic progenitors on the basis of aldehyde dehydrogenase activity. Proceedings of the National Academy of Sciences, 96(16), 9118-9123). The Aldefluor™ kit assay was used according to the procedure described by the manufacturer. Briefly, MOLM-14 cell line was cultured in MEM alpha medium supplemented with 10% v/v Fetal Bovine Serum, 1% Penicillin-Streptomycin and maintained at 37° C. with 5% $CO_2$. $5·10^5$ cells were used in this assay. Each compound was added at different concentrations (see table 8), and cell cultures were incubated for 72 h. Vehicle ($H_2O$) was used as a control, and all compounds were tested in a constant percentage of vehicle. Cells obtained from cell culture were incubated for 45 minutes at 37° C. with Aldefluor™ buffer assay containing the Bodipy™-aminoacetaldehyde, a fluorescent ALDH aldehyde substrate. ALDH converts the fluorescent substrate BAAA to the Bodipy™-aminoacetic acid (BAA) which is retained in the cell. An active efflux inhibitor is present in the Adelfluor™ assay buffer in order to avoid the active efflux from the cell of the substrate product ALDH dependent converted BAA. The fluorescent signal is directly proportional to the ALDH activity in the cells and is measured by flow cytometry. A negative control is used to measure the background fluorescence level. For such purpose, 4-(N,N-diethylamino)-benzaldehyde (DEAB) was used as selective ALDH inhibitor. A viability cell count was performed using LIVE/DEAD® Fixable Far Red Dead Cell Stain Kit (Invitrogen). The experimental data are analyzed using a computer program, Graphpad Prism v5 (GraphPad Software, Inc. La Jolla, Calif.) and $EC_{50}$ values were determined as the dose of compound required to reduce absorbance values to 50% of the signal obtained for vehicle treated cell cultures.

TABLE 7

Growth inhibition assay of MOLM-14 cell line in presence of Cytarabin and compound 2-3

| Compounds | Cytarabin | 2-3[a] |
|---|---|---|
| $EC_{50}$ (µM) | 0.290 | 2.2 |

[a]$EC_{50}$ were obtained from the method described in example 5 see table 3

TABLE 8

ALDH population decreases in MOLM-14 cell line by compound 2-3 using Aldefluor™ kit assay

| Compounds | Control | Cytarabin | | 2-3 | | |
| | | 1 µM | 3 µM | 2.5 µM | 5.0 µM | 7.5 µM |
|---|---|---|---|---|---|---|
| ALdefluor™ positive CSCs (%) | 100 | 130 | 116 | 100 | 80 | 20 |

7. Example 7: Growth Inhibition Assay ($EC_{50}$, µM) of Hep3B-Luc Cell Line in Presence of Compound 2-3

Before compound treatment, the compound was dissolved in $H_2O$ to make a 10 mM stock solution. The working solutions (5 folds final concentrations) were then prepared with MEM medium (Gibco, 1128319) containing 10% Fetal Bovine Serum (Gibco, 10099141).

When performing the assay, dose response test of Doxorubicin on BEL-7402 cells line (human primary hepatocellular carcinoma) will be used as internal control in each assay plate for the assay. The MEM medium supplemented with 5% $H_2O$ (5×) will be added into the cells as a negative controls. The final $H_2O$ concentration was 1% in each well.

Hep3B-Luc cell line (luciferase transfected human liver carcinoma cell line for orthotopic tumor model) was cultured in MEM Medium supplemented with 10% v/v Fetal Bovine Serum (FBS), 1% Penicillin-Streptomycin and maintained at 37° C. with 5% $CO_2$. 800 cells were plated onto 384-well flat clear bottom white (Corning, 3707).

Assay Procedure:

Cells in log-phase are collected and counted. Cell suspensions are added to each well of 384-well plate at 800 cells per well (total volume 40 µl). The margin wells are filled with PBS buffer. Test compound at various concentrations are added in duplicates (add 10 µl 5× compound solutions to the plate). The assay plate is incubated for 72 h in 37° C./5% $CO_2$ incubator. Cell viability was measured using the CellTiter-Glo® luminescent cell viability assay as described by the manufacturer (Promega, Ref G7571). After addition of 100 µL of CellTiter-Glo® reactifs solution, luminescence was measured using a PHERAstar Plus luminometer. Data were recorded by PHERAstar Plus, Data acquisition and analysis were performed using Microsoft Excel program and GraphPad Prism v.6 software.

TABLE 9

Growth inhibition assay of Hep3B-Luc cell line in presence of compound 2-3

| Compounds | Doxorubicin | 2-3 |
|---|---|---|
| Cell lines | BEL-7402 | Hep3B-Luc |
| $EC_{50}$ (µM) | 0.15 | 1.1 |

8. Example 8: Grow Inhibition Assay (EC$_{50}$, μM) of CAKI-1 and 786-0 Cell Lines in Presence of Compound 2-3

Cell Culture:

CAKI-1 and 786-0 cell lines were maintained in RPMI 1640 medium (Dutscher, L0498) containing 1% penicillin-streptomycin (Dutscher, P06-07100) and 10% Fetal Bovine Serum (Gibco, W3387L) and cultured at 37° C. with 5% $CO_2$.

Cell Viability Measures:

Cell viability was measured using the CellTiter-Glo® luminescent cell viability assay as described by the manufacturer (Promega, Ref G7571) using an Infinite F200Pro luminometer (Tecan). Briefly, cells were plated onto 96-well plates (white with clear bottom) in 90 μL of media per well and were allowed to grow overnight before the assay. The number of cells seeded per well is indicated in the table below:

TABLE 10

Number of cell seeded per well for CAKI-1 and 786-O cell viability assays

| | Cell number per well |
|---|---|
| CAKI-1 | 2250 |
| 786-O | 1250 |

Compounds 2-3 and two reference compounds (Sorafenib and Sunitinib) were added at different concentrations to each well, and cell cultures were incubated for 72 h. For compound 2-3 analysis, $H_2O$ was used as a negative control (=untreated) and all concentrations were tested in a constant percentage of $H_2O$. For Sorafenib and Sunitinib analysis, DMSO was used as a negative control (=untreated) and all concentrations were tested in a constant percentage of DMSO. 72 h after incubation of compounds, 100 μL of CellTiter-Glo® were added to each well and luminescence was measured using an Infinite F200Pro (Tecan). EC$_{50}$ values were determined as the dose of compound required to reduce luminescent values to 50% of the signal obtained for untreated cell cultures. The experimental data were analyzed using a computer program, Graphpad Prism v5 (GraphPad Software, Inc. La Jolla, Calif.). All experiments were at least done in triplicate and repeated at least three independent times.

TABLE 11

Growth inhibition assay of CAKI-1 cell line in presence of compound 2-3 and Sorafenib, Sunitinib as controls

| Compounds | EC$_{50}$ (μM) | SD |
|---|---|---|
| 2-3 | 1.4 | 0.1 |
| Sorafenib | 4.5 | 1.5 |
| Sunitinib | 1.7 | 0.7 |

TABLE 12

Growth inhibition assay of 786-O cell line in presence of compound 2-3 and Sorafenib, Sunitinib as controls

| Compound | EC$_{50}$ (μM) | SD |
|---|---|---|
| 2-3 | 2.1 | 0.2 |
| Sorafenib | 6.8 | 1.7 |
| Sunitinib | 6.0 | 1.1 |

9. Example 9: In Vitro Effect of Compound 2-3 on Liver Metastatic Colon Cancer Cells and Subpopulation of Colon Cancer Stem Cells The aim of this study was to evaluate in vitro the cytotoxic activity of compound 2-3 against liver metastatic colon cancer patient derived cells freshly isolated from patients and more specifically on the CSCs subpopulation. Few methods are currently available to track in vitro the CSCs. For instance, aldehyde dehydrogenase (ALDH) activity can be used as a marker to identify cancerous human stem cells in colon cancer. In addition, CSC can be enriched by cultivating cells in suspension into a serum-free medium supplemented with growth factors. In such conditions, only CSCs grew as multicellular three-dimensional clones called "tumorospheres". By taking advantage of tumorosphere-forming ability we can then estimate the amount of CSCs in the sample and thus assess the effect of a given molecule on the CSCs ability to self-renew.

Patient-Derived Tumor Cells Culture

Patient derived liver metastasis cells (CPP19, 30, 36 and CPP45—see table 1 for clinical descriptions) were maintained in complete DMEM (Gibco) with 10% FBS. Cells were obtained from biopsies provided by CHU-Caremeau (Nimes, France) within an approved protocol. Signed informed consents were obtained from patients prior to samples acquisition in accordance with all ethical and legal aspects. Tumors were washed, minced into fragments (<2 mm$^3$) and digested with liberase H (0.26 U/mL, Roche) resuspended in Accumax (Sigma-Aldrich). After 2 hours at 37° C., cell suspension was filtered through a 40 m mesh to obtain a single cell suspension and plated in DMEM medium, supplemented with FBS, glutamine, antibiotics and non-essential aminoacids. When a monolayer of patient-derived tumor cells was formed, cells were detached using trypsin/EDTA and resuspended in DMEM with 10% FBS (for adherent cells) or defined M11 media (for sphere formation). Cells were cultured in a humidified atmosphere at 37° C. and 5% $CO_2$.

In Vitro Toxicity Assays

Cells were plated at 10$^4$ cells per well in P96 well plates in DMEM with 10% FBS. After 24 hours, cells were treated with compound 2-3 and cell viability was assessed 72 h post-treatment by CellTiter-Glo® Luminescent Cell Viability Assay (Promega). EC$_{50}$ were calculated using GraphPad Prism Software v6 (Graphpad Software, Inc La Jolla, Calif.).

Aldefluor™ assay and fluorescence-activated cell sorting (FACS) The Aldefluor™ assay (Stem Cell Technologies, 01700) was performed according to the manufacturer's instructions (Stem Cell Technologies). ALDH$^{positive}$ cells were identified by comparing the same sample with and without the ALDH inhibitor diethylaminobenzaldehyde (DEAB). FACS gating of ALDH activity was set at 0.1% in presence of DEAB. Cells were analyzed using MacsQuant and data analyzed using Cyflogic software. CPP36 cells were not used in these analyses because of their high cellular autofluorescence profile.

Sphere Formation Assays

Evaluation of Cell Forming Sphere was determined after plating 500 cells/200 μL well in M11 medium in P96 wells in ultra-low attachment plates (Corning). M11 is DMEM/F12 (1:1) medium (Gibco), supplemented with N2, Glutamine 3 mM, Glucose 0.6%, insulin 4 μg/ml (Sigma-Aldrich), hBasic-FGF 10 ng/ml (R&D Systems), and hEGF 20 ng/ml (R&D Systems). Sphere size exceeding 50 μm were counted after 10 days and represented at number of spheres per image field. CPP45 cells were not used in these analyses because of their inability to form tumorospheres.

Statistical Analysis

For each experiment, data are shown as mean S.E.M of three independent experiments. GraphPad Prism Software v6 (Graphpad Software, Inc La Jolla, Calif.). was used for data analysis, i.e. student's t-tests.

TABLE 13

Clinical characteristics of colon cancer patient

|  | CPP19 | CPP30 | CPP36 | CPP45 |
|---|---|---|---|---|
| Gender | M | M | M | M |
| Age | 65 | 69 | 81 | 80 |
| Mutation | KRAS | None | KRAS | KRAS |
| TNM classification | T3N2aM1 | TxNxM1 | T4N2bM1 | T3N1cM1 |
| Radiotherapy | None | None | None | None |
| Chemotherapy | Bevacizumab, folfiri | Bevacizumab Folfox, Folfiri Xelox | Bevacizumab & folfiri | None |

In Vitro Evaluation of Cytotoxicity of Compound 2-3 on Liver Metastatic Colorectal Cancer (CRC) Patient-Derived Cells CellTiter-Glo® Luminescent Cell Viability Assay, as described by the manufacturer (Promega, Ref G7571), was used to determine the cytotoxicity of compound 2-3 in liver metastatic CRC patient-derived cells. The cell viability from untreated control cells is set at 100%. Cells were first plated at a density of 10.000 cells/100 µL per well in P96 plates and incubated in a humidified atmosphere with 5% $CO_2$ at 37° C. for 24 hours. Cells were then incubated with solvent (0.1% DMSO, untreated control cells) or increasing concentration of compound 2-3. After 72 hours of incubation at concentration ranging from 0.1 to 30 µM, compound 2-3 demonstrated a dose-response cytotoxic activities against four different CRC patient-derived cells established from fresh liver metastasis biopsies (Table 14).

TABLE 14

Growth inhibition assay on liver metastatic CRC patient-derived cells in presence of compound 2-3

| CRC ID | CPP19 | CPP30 | CPP36 | CPP45 |
|---|---|---|---|---|
| $EC_{50}$ (µM) | 1.88 | 1.22 | 1.45 | 1.12 |

In Vitro Evaluation of Compound 2-3 on Aldefluor™ Positive Cells from Liver Metastatic CRC Patient-Derived Cells Cells were first plated at a density of 250.000 cells/1000 µL per well in P96 plates and incubated in a humidified atmosphere with 5% $CO_2$ at 37° C. for 24 hours. Cells were then incubated with solvent (0.1% DMSO) or increasing concentration of compound 2-3 for 72 hours. The cells were trypsinized, collected, and washed. A cellular particles and dead cells were excluded based on low light scatter and Sytox Blue dead cell stain positivity (Life Technologies) using a MACSQuant flow cytometer (Miltenyi biotec). The percentage of $ALDH^{bright}$ cells was then quantified using the Aldefluor™ assay (Stemcell Technologies, 01700). The ALDH inhibitor, diethylaminobenzaldehyde (DEAB), was added to ensure the accurate identification of ALDH-positive cells. When the ALDH inhibitor DEAB was applied, fluorescence was reduced (shifted to the left) and a gate was drawn to delineate the upper limit of these cells. This gate was used to select for the ALDH high-staining subpopulation. As shown, after 72 hours of incubation at concentration ranging from 1 to 3 µM, compound 2-3 demonstrates a significant (p<0.001) and dose-response cytotoxic activities against the Aldefluor™ positive cell subpopulation in three different CRC patient-derived cells established from fresh liver metastasis biopsies (FIG. 1).

Compound 2-3 Blocks Tumorosphere Formation of Liver Metastatic CRC Patient-Derived Cells.

Figure 2:
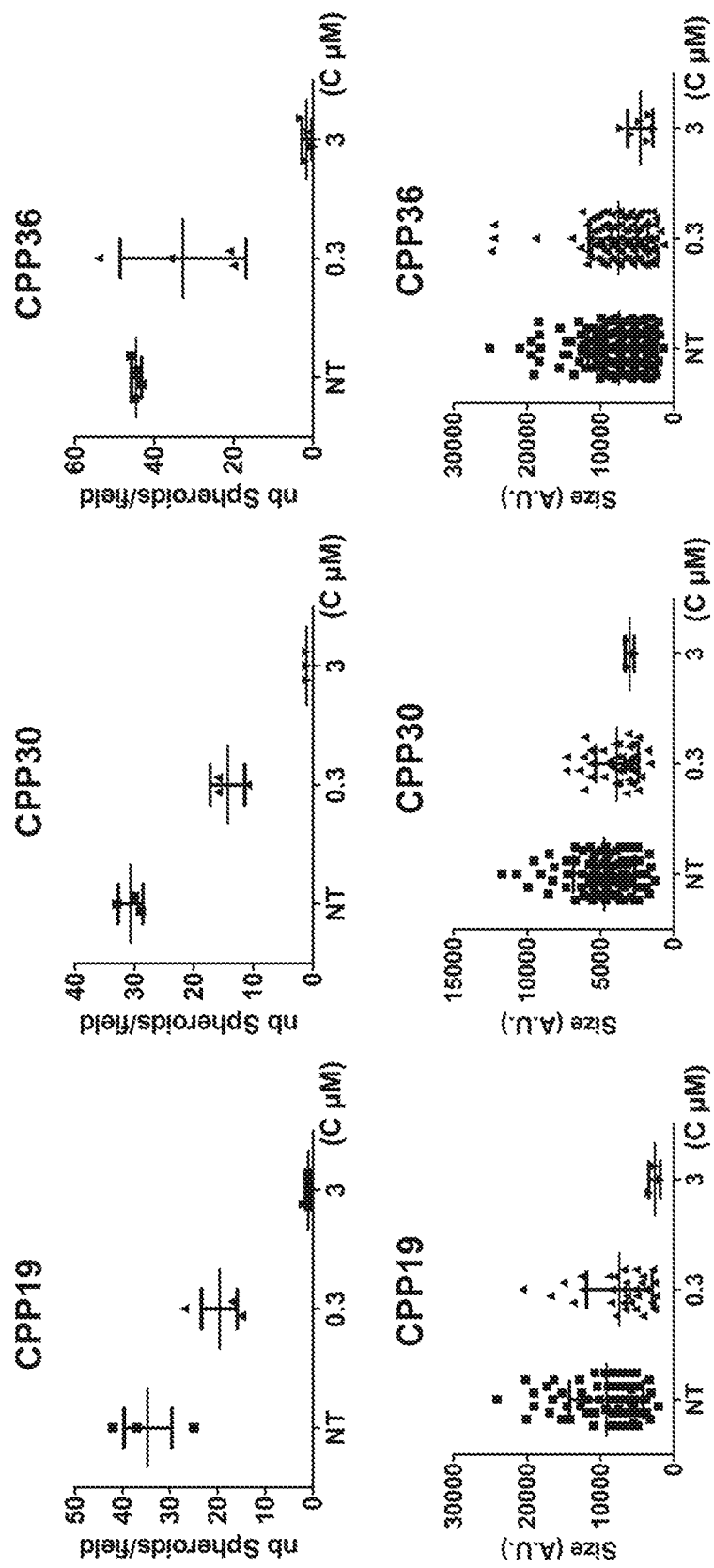
FIG. 2 shows the inhibition, by compound 2-3, of tumorosphere formation of liver metastatic colorectal cancer (CRC) patient derived cells.
Figure 3:
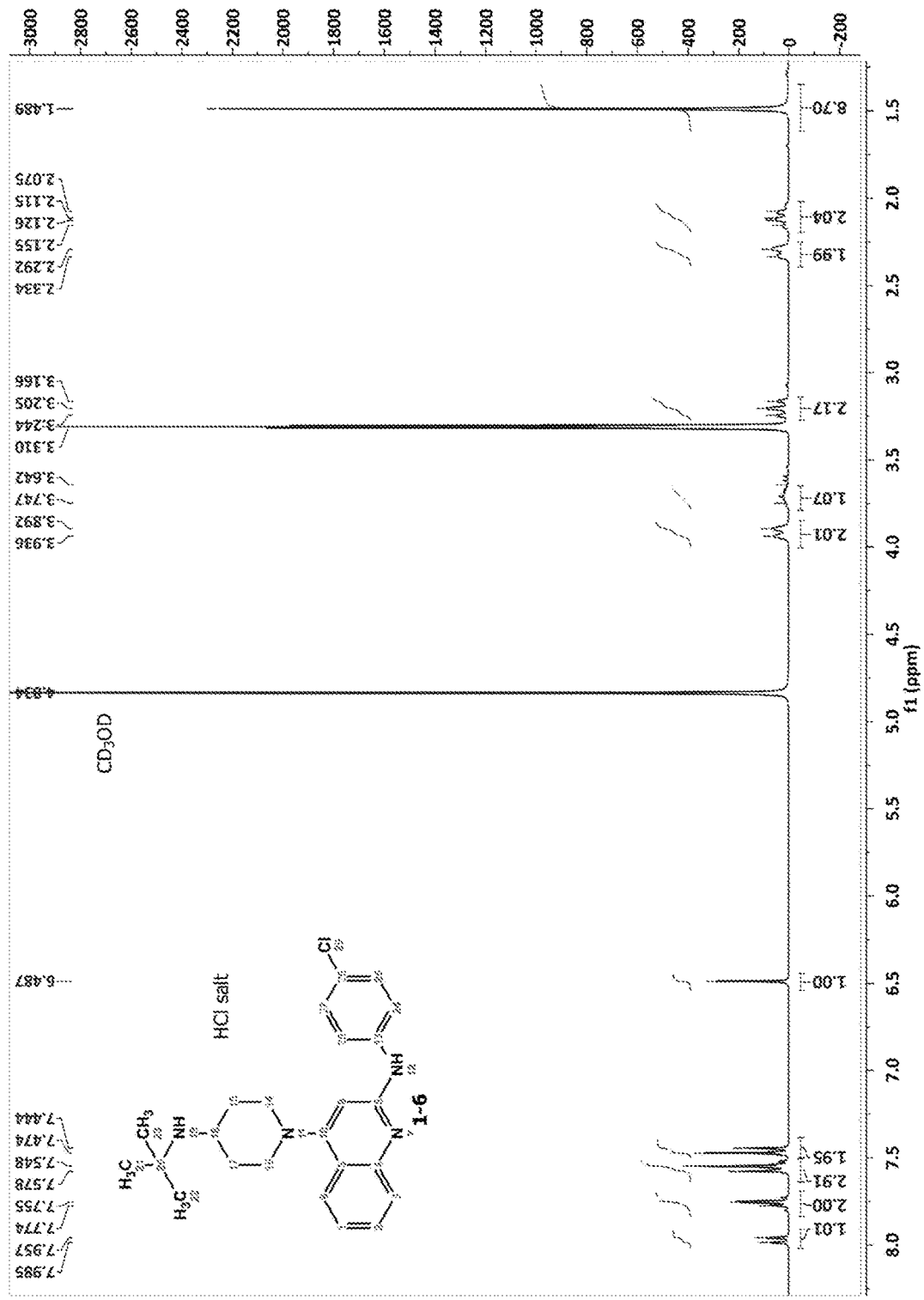
FIG. 3 shows the $^1$H NMR spectra of compound 1-6 in DMSO-$d_6$.
Figure 4:
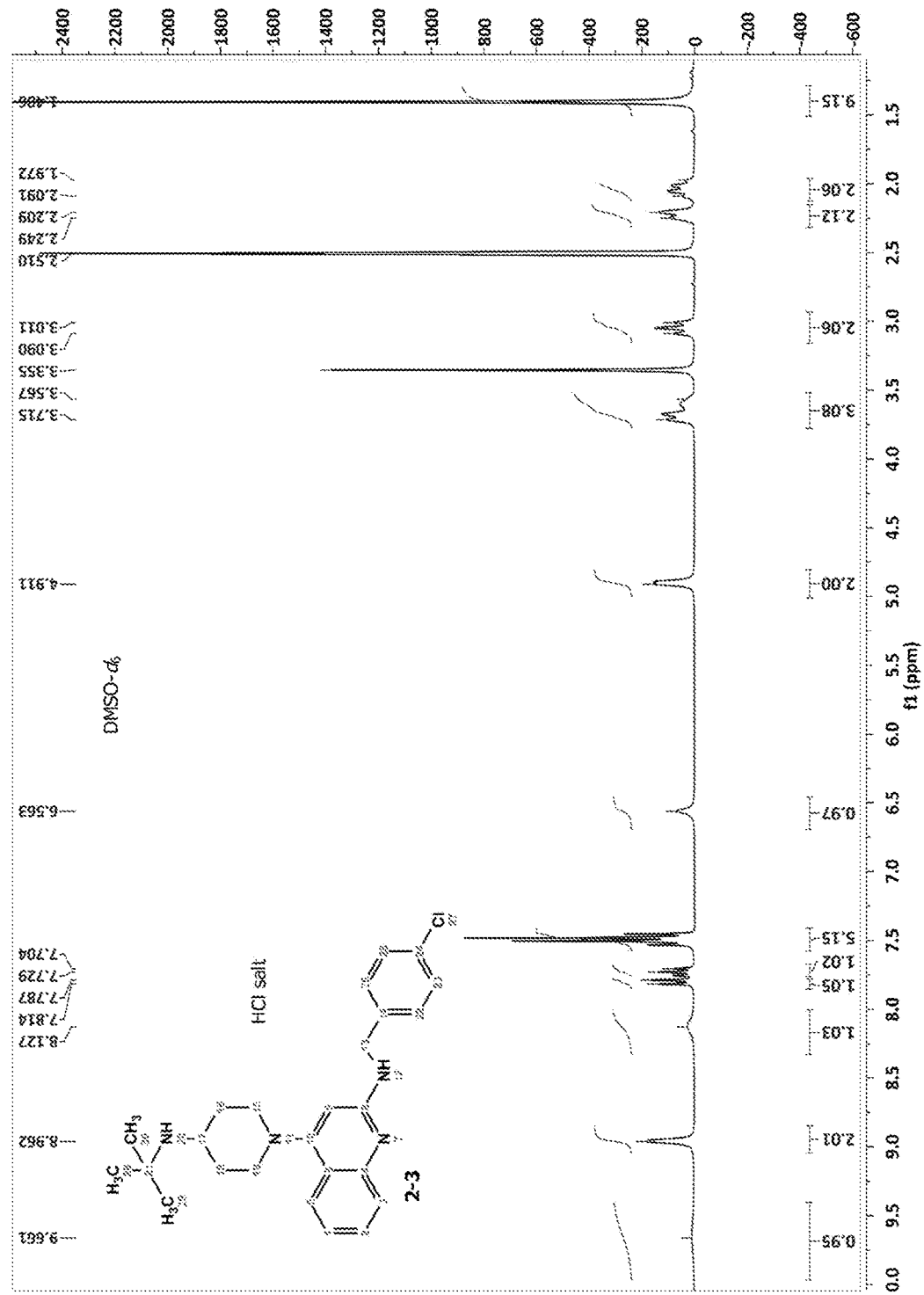
FIG. 4 shows the $^1$H NMR spectra of compound 2-3 in DMSO-$d_6$.
Figure 5:
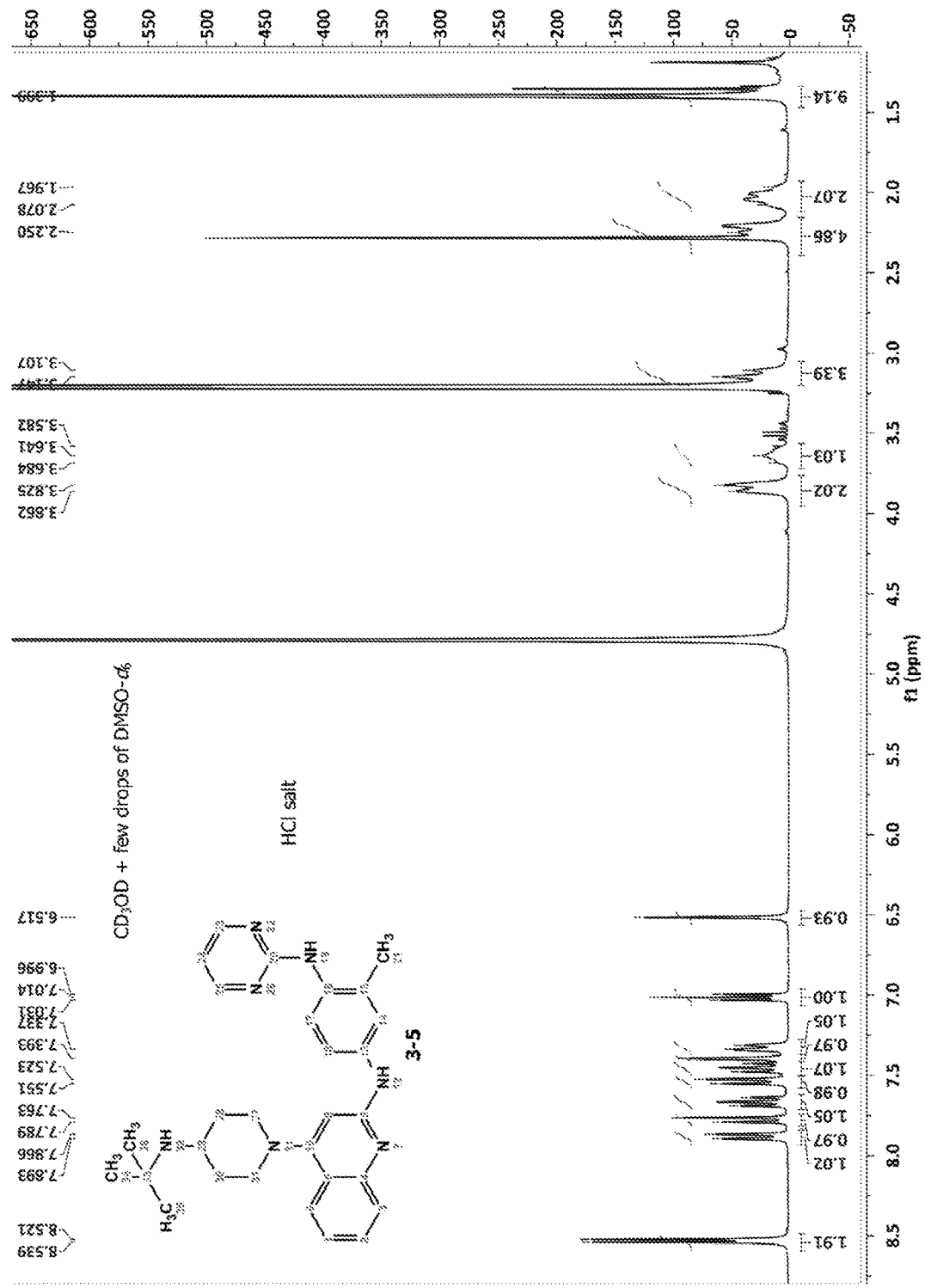
FIG. 5 shows the $^1$H NMR spectra of compound 3-5 in DMSO-$d_6$.
Figure 6:
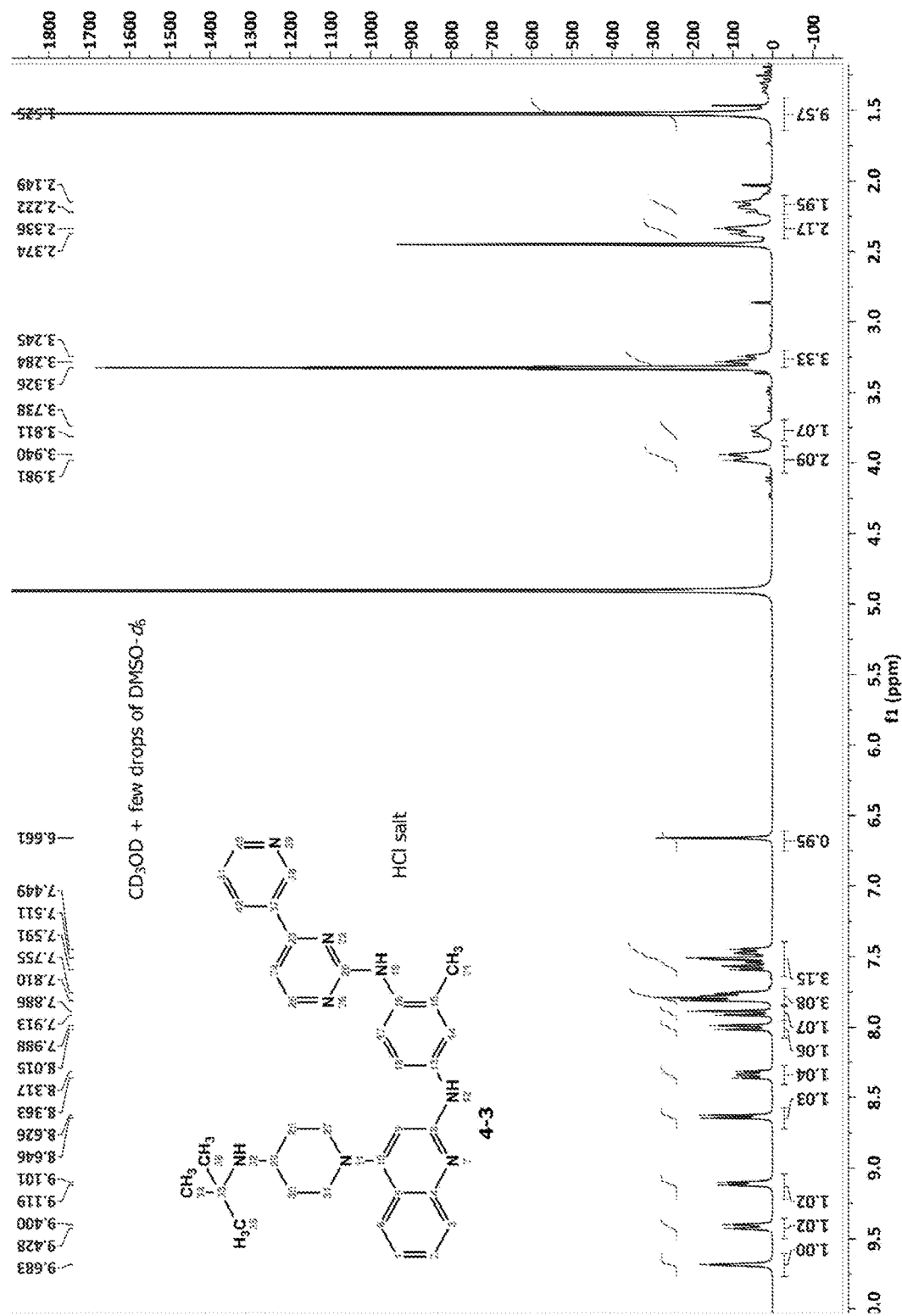
FIG. 6 shows the 1H NMR spectra of compound 4-3 in DMSO-$d_6$.

In vitro tumorosphere formation is widely used to identify the presence of cancer stem cells (CSCs) in solid tumors or heterogeneous cell populations, since only these cells have the ability to self-renew. We used this assay as a functional measure of CSC frequency and viability, and examined the ability of liver metastasis patient derived cells to form tumorospheres after treatment with compound 2-3. For this purpose, cells were first grown in tissue culture flask with DMEM Complete medium with fetal bovine serum (FBS) as a monolayer until they reached near confluency. The cells were trypsinized, collected, washed to remove the FBS and passed through a 40 µm mesh cell strainer. Single-cell suspension was then cultured with CSC medium (i.e. M11 medium) consisting of DMEM-F12 supplemented with 20 ng/ml EGF, 20 ng/ml bFGF and N2 supplement (Invitrogen, Carlsbad, Calif., USA) in P96 well ultra-low attachment plate (Corning Life Sciences, Tewksbury, Mass.). Cells were plated at a density of 500 cells/100 µL per well and incubated in a humidified atmosphere with 5% $CO_2$ at 37° C. To determine the effect of compound 2-3 on tumorosphere forming efficiency and sphere size, compound 2-3 was added at two concentrations (0.3 µM or 3 µM) 24 hours after plating in a final volume of 200 µL of M11. Ten days later, plates were examined for tumorosphere formation (>50 µm) using an inverted microscope. Phase contrast pictures were taken and sphere size and number were manually measured and counted from the images using ImageJ. As shown in FIG. 2, compound 2-3 induced a drastic and dose-dependent decrease in tumorosphere formation in the three tested CRC patient derived cells isolated from hepatic metastases (CPP19, CPP30 and CPP36). Indeed, the tumorosphere forming efficiency was significantly suppressed by 3 µM of compound 2-3. In contrast, the size of tumorospheres was not statistically decreased by the treatment, except at 3 µM on CPP19 cells (p=0.02).

Example 10: Growth Inhibition Assay (ECo, 1 µM) of Hepatocellular Carcinoma (HCC) Patient Derived Cell in Presence of Compound 2-3

The patient derived Hepatocellular Carcinoma (HCC) cells were obtained after written informed consent under the CrownBio institutional review board approval and under the strict compliance of the Helsinki declaration on medical research involving human subjects.

The patient derived Hepatocellular Carcinoma (HCC) cells were maintained in medium respectively described in table 15 containing 1% penicillin-streptomycin (Life Technologies, 15070-063), with a supplements for primary cell culture (PCS) containing hydrocortisone (50 nM), Epidermal Growth Factor (20 ng/ml), β-fibroblast Growth Factor (10 ng/ml), Heparin (2 μg/ml) ITS liquid media supplement (1×) and non-essential amino acid (NEAA, 0.01 mM, 1×). The primary cell were cultured in a humidified atmosphere (95% relative humidity) with 5% $CO_2$ at 37° C.

TABLE 15

Culture medium and culture condition for patient derived Hepatocellular Carcinoma (HCC) cells

| Entry | Primary Cell | Culture medium | Culture condition |
|---|---|---|---|
| 1 | LI0050 | DMEM/F12 + 10% FBS + PCS | 37° C., 5% $CO_2$, 95% relative humidity |
| 2 | LI0574 | DMEM/F12 + 10% FBS + PCS | 37° C., 5% $CO_2$, 95% relative humidity |
| 3 | LI0612 | DMEM/F12 + 10% FBS + PCS | 37° C., 5% $CO_2$, 95% relative humidity |
| 4 | LI0752 | DMEM/F12 + 10% FBS + PCS | 37° C., 5% $CO_2$, 95% relative humidity |
| 5 | LI0801 | DMEM/F12 + 10% FBS + PCS | 37° C., 5% $CO_2$, 95% relative humidity |
| 6 | LI1005 | DMEM/F12 + 10% FBS + PCS | 37° C., 5% $CO_2$, 95% relative humidity |
| 7 | LI1098 | DMEM/F12 + 10% FBS + PCS | 37° C., 5% $CO_2$, 95% relative humidity |
| 8 | LI1646 | DMEM/F12 + 10% FBS + PCS | 37° C., 5% $CO_2$, 95% relative humidity |

The cell growth inhibition assay was performed as described previously in example 5 using the CellTiter-Glo® luminescent cell viability assay as described by the manufacturer (Promega, Ref G7571). The number of cells seeded per well (in 96-Well Flat Clear Bottom Black Polystyrene TC-Treated Microplates, Cat #3340, Corning®) is described in the table 16. A backseal black sticker (Cat #6005189, Perkin Elmer) was placed to the bottom of each plate before recording CellTiter-Glo® luminescence.

TABLE 16

Number of cells seeded per well for HCC Patient derived cell viability assays

| Entry | HCC Patient derived cells | Cell number per well |
|---|---|---|
| 1 | LI0050 | 2,500 |
| 2 | LI0574 | 3,000 |
| 3 | LI0612 | 4,000 |
| 4 | LI0752 | 3,500 |
| 5 | LI0801 | 2,500 |
| 6 | LI1005 | 2,500 |
| 7 | LI1098 | 2000 |
| 8 | LI1646 | 2000 |

The experimental data are analyzed using a computer program, Graphpad Prism V 5.0 (GraphPad Software, Inc. La Jolla, Calif.) and $EC_{50}$ values were determined as the dose of compound required to reduce absorbance values to 50% of the signal obtained for vehicle treated cell cultures and were a mean of at least three independent experiments.

After 72 hours of incubation, compound 2-3 demonstrated a dose-response cytotoxic activities against eight different HCC patient derived cells (see table 17).

TABLE 17

Growth inhibition assay on Hepatocellular Carcinoma (HCC) patient-derived cells in presence of compound 2-3, Sorafenib and Cisplatin

| | HCC Patient | $EC_{50}$ (μM) | | |
|---|---|---|---|---|
| Entry | derived cells | 2-3 | Sorafenib | Cisplatin |
| 1 | LI0050 | 3.5 | 9.1 | 1.3 |
| 2 | LI0574 | 2.4 | 8.7 | 3.6 |
| 3 | LI0612 | 6.9 | 17.9 | 16.3 |
| 4 | LI0752 | 0.5 | 6.3 | 2.6 |

TABLE 17-continued

Growth inhibition assay on Hepatocellular Carcinoma (HCC) patient-derived cells in presence of compound 2-3, Sorafenib and Cisplatin

| | HCC Patient | $EC_{50}$ (μM) | | |
|---|---|---|---|---|
| Entry | derived cells | 2-3 | Sorafenib | Cisplatin |
| 5 | LI0801 | 2.1 | 5.7 | 1.5 |
| 6 | LI1005 | 3.2 | 14.5 | 5.9 |
| 7 | LI1098 | 7.0 | 10.9 | 5.1 |
| 8 | LI1646 | 1.4 | 10.3 | 10.0 |

The invention claimed is:
1. A compound of formula (I)

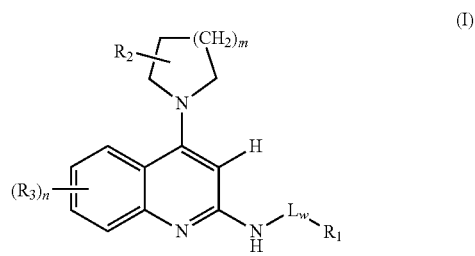

Wherein
$R_1$ is chosen from a C6-C10 aryl substituted or not by $R_9$; a heteroaryl 5 to 8-membered ring comprising 1, 2, 3 heteroatoms selected from O, N and S substituted or not by $R_9$; a fused heteroaryl as defined comprising from 8 to 13 atoms including 1, 2, 3, 4, heteroatoms selected from O, N and S and comprising at least 2 carbon atoms substituted or not by $R_9$;
L is chosen from an optionally substituted (C1-C10) alkyl; a (C1-C10) alkyl linear or branched substituted by $R_4$; an optionally substituted (C3-C10) cycloalkyl; an optionally substituted (C5-C10) cycloalkenyl; an optionally substituted (C3-C10) alkenyl; an optionally substituted (C3-C10) alkynyl; C=O; SO; $SO_2$; (C=O)—$NR_8$; (C=O)—O; (C=O)—O—(C1-C4) alkyl; $SO_2NR_8$; $NR_8$; wherein $R_4$ is chosen from H; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; an optionally substituted (C6-C10) aryl; an heteroaryl 5 to 8-membered ring or a fused heteroaryl as defined comprising from 8 to 13 atoms including 1, 2, 3, 4 heteroatoms selected from O, N and S and comprising at least 2 carbon atoms substituted or not with one or more substituent groups independently selected from hydrogen, halogen atom, (C1-C10) alkyl substituted with by one or more halogens atom(s), (C1-C10) alkoxy, hydroxyl, cyano, nitro, carboxy, $NR_8R_8'$, a 4 to 9-membered ring saturated or unsaturated comprising 1, 2 or until 3 heteroatoms independently selected from O, N and S;

$R_2$ is selected from $NR_5R_6$;

$R_3$ is chosen from a hydrogen atom; a halogen atom; a (C1-C10) alkyl linear or branched substituted or not by one or more halogen atom(s), hydroxyl, alkoxy-$NR_5R_6$; a (C2-C10) alkenyl; a (C2-C10) alkynyl; a (C3-C10) cycloalkyl; a (C5-C10) cycloalkenyl; a (C8-C10) cycloalkynyl; a (C1-C10) alkoxy; a hydroxyl; a nitro; a cyano; a $NR_5R_6$; a O—($R_7$); a (CO)—$R_7$; a (CO)—O—$R_7$; a (CO)—$NR_5R_6$; a O—(CO)—$R_7$; a O—(CO)—$NR_5R_6$; a $NR_5$—(CO)—$R_7$; a $NR_5$—(CO)—$OR_7$; a $NR_5$—(CO)—$NR_5R_6$; a —(O—$CH_2CH_2$-)$_m$-ORn; a -(O-$CH_2CH_2$-)$_m$-$NR_{11}R_{11'}$; a $SO_2$—$R_7$; a $NR_5$—$SO_2$—$R_7$; a $SO_2$—$NR_5R_6$; a $NR_5$—($C_2$-$C_6$)-alkyl-$NR_5R_6$; an optionally substituted aryl; an optionally substituted benzyl; an optionally substituted heteroaryl from 5 to 8-membered ring comprising 1, 2, or 3 heteroatoms selected from O, N and S; an optionally substituted fused heteroaryl as defined comprising from 8 to 13 atoms including 1, 2, 3, 4 heteroatoms selected from O, N and S and comprising at least 2 carbon atoms; an optionally substituted heterocyclyl from 4 to 9-membered ring saturated or unsaturated comprising 1, 2 or until 3 heteroatoms independently selected from O, N and S;

$R_5$ and $R_6$ are independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; a (CO)—$R_7$; a (CO)—O—$R_7$; a (CO)—$NR_8R_8'$; a $SO_2$—$R_7$; a $SO_2$—$NR_8R_8'$; a (C1-C10) alkyl substituted with $NR_8R_8'$; a (C3-C10) cycloalkyl substituted with $NR_8R_8'$; an optionally substituted aryl; an optionally substituted benzyl; an optionally substituted heteroaryl 5 to 8-membered ring comprising 1, 2, or 3 heteroatoms selected from O, N and S; an optionally substituted heterocyclyl from 4 to 9-membered ring saturated or unsaturated comprising 1, 2 or until 3 heteroatoms independently selected from O, N and S; or $R_5$ and $R_6$ is linked together with the nitrogen atom to which they are covalently linked to form a heterocyclyl group forming a 4 to 9-membered ring which may contain additional 1, 2, or 3 heteroatoms selected from O, N and S;

$R_7$ and $R_{7'}$ are independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; a C1-C10 linear or branched alkyl substituted with $NR_8R_8$; an optionally substituted (C6-C10) aryl, an optionally substituted benzyl, an optionally substituted heteroaromatic 5 to 8-membered ring comprising 1, 2, or 3 heteroatoms selected from O, N and S;

$R_8$ and $R_{8'}$ are independently chosen from a hydrogen; an optionally substituted (C1-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; or $R_8$ and $R_{8'}$ is linked together with the nitrogen atom to which they are covalently linked to form a heterocyclyl group forming a 4 to 9-membered ring which may contain additional 1, 2, or 3 heteroatoms selected from O, N and S;

$R_9$ is independently selected from a hydrogen; a halogen atom; an optionally substituted (C1-C10) alkyl; an (C1-C10) alkyl linear or branched substituted by one or more halogen atom(s), a hydroxyl, an alkoxy; an optionally substituted (C2-C10) alkenyl; an optionally substituted (C2-C10) alkynyl; an optionally substituted (C3-C10) cycloalkyl; an optionally substituted (C5-C10) cycloalkenyl; an optionally substituted (C8-C10) cycloalkynyl; an optionally substituted (C1-C10) alkoxy; a hydroxyl; a nitro; a cyano; a $NR_5R_6$, a (CO)—$R_7$; a (CO)—O—$R_7$; a (CO)—$NR_5R_6$; a O—(CO)—$R_7$; a O—(CO)—$NR_5R_6$; a $NR_5$—(CO)—$R_7$; a $NR_5$—(CO)—$OR_7$; a $NR_5$—(CO)—$NR_5R_6$; a $SO_2$—$R_7$; a $NR_5$—$SO_2$—$R_7$; a $SO_2$—$NR_5R_6$; a (C1-C10) alkyl substituted with $NR_5R_6$; a $NR_5$—(C2-C10)-alkyl-$NR_5R_6$; a —(O—$CH_2CH_2$-)$_m$-$OR_{11}$; a —(O—$CH_2CH_2$-)m-$NR_{11}R_{11'}$; an optionally substituted (C6-C10) aryl; an optionally substituted benzyl; an optionally substituted heteroaryl 5 to 8-membered ring comprising 1, 2, or 3 heteroatoms selected from O, N and S; an optionally substituted heterocyclyl group forming a 4 to 9-membered ring which may contain 1, 2, or 3 heteroatoms selected from O, N and S; a —$NR_5R_{10}$; a —O—$R_{10}$;

$R_{10}$ is independently chosen from a hydrogen; a (C6-C12)-aryl substituted or not by $R_{12}$; a benzyl substituted or not by $R_{12}$; a heteroaryl from 5 to 8-membered ring comprising 1, 2, or 3 heteroatoms selected from O, N and S substituted or not by $R_{12}$; a fused heteroaryl defined as comprising from 8 to 13 atoms including 1, 2, 3, 4 heteroatoms selected from O, N and S and comprising at least 2 carbon atom substituted or not by $R_{12}$; a heterocyclyl forming a 4 to 9-membered ring which can contain 0, 1, 2, or 3 heteroatoms selected from O, N and S substituted or not by $R_{12}$;

$R_{11}$ and $R_{11'}$ is independently chosen from a hydrogen atom; an optionally substituted (C2-C10) alkyl; an optionally substituted (C3-C10) alkenyl; an optionally substituted (C3-C10) alkynyl; an optionally substituted (C3-C10) cycloalkyl; an optionally substituted (C5-C10) cycloalkenyl; an optionally substituted (C8-C10) cycloalkynyl; an (C2-C10) alkyl linear or branched substituted or not by one or more halogen atom(s); or $R_{11}$ and $R_{11'}$ is linked together with the nitrogen atom to which they are covalently linked to form a heterocyclyl group forming a saturated or unsaturated 4 to 9-membered ring which may contain additional 1, 2, or 3 heteroatoms selected from O, N and S;

$R_{12}$ is chosen from a hydrogen atom; a halogen atom; a (C1-C10) alkyl linear or branched substituted or not by one or more halogen atom(s), hydroxyl, alkoxy, $NR_{11}R_{11}$; a (C2-C10) alkenyl; a (C2-C10) alkynyl; a (C3-C10) cycloalkyl; a (C5-C10) cycloalkenyl; a (C8-C10) cycloalkynyl; a (C1-C10) alkoxy; a hydroxyl; a nitro; a cyano; a $NR_{11}R_{11}$; a O—($R_7$); a (CO)—$R_7$; a (CO)—O—$R_7$; a (CO)—$NR_{11}R_{11}$, a O—(CO)—$R_7$; a O—(CO)—$NR_{11}R_{11}$; a $NR_{11}$—(CO)—$R_7$; a $NR_{11}$—(CO)—$OR_{11}$; a $NR_{11}$—(CO)—$NR_{11}R_{11}$; a —(O—$CH_2CH_2$-)$_m$-$OR_{11}$; a —(O—$CH_2CH_2$-)$_m$-$NR_{11}R_{11}$; a $SO_2$—$R_7$; a $NR_5$—$SO_2$—$R_7$; a $SO_2$—$NR_{11}R_{11}$; a $NR_{11}$—(C2-C6)-alkyl-$NR_{11}R_{11}$; an optionally substituted aryl; an optionally substituted benzyl; an optionally substituted heteroaryl from 5 to 8-membered ring comprising 1, 2, or 3 heteroatoms selected from O, N and S; an optionally substituted fused heteroaryl as defined comprising from 8 to 13 atoms including 1, 2, 3, 4 heteroatoms selected from O, N and S and comprising at least 2 carbon atoms; an optionally substituted heterocyclyl from 4 to 9-membered ring saturated or unsaturated comprising 1, 2 or until 3 heteroatoms independently selected from O, N and S;

n can represent an equal integer which can have any one of the values 0, 1, 2, 3 or 4;

m can represent an equal integer which can have any one of the values 1, 2 or 3;

w can represent an equal integer which can have any one of the values 0 or 1;

wherein the term "optionally substituted" means optionally substituted with one or more substituents independently chosen from an halogen atom, a (C1-C10) alkyl linear or branched substituted or not by one or more halogen atom(s), a (C2-C10) alkenyl linear or branched substituted or not by one or more halogen atom(s), a (C2-C10) alkynyl linear or branched substituted or not by one or more halogen atom(s), a (C3-C10) cycloalkyl substituted or not by one or more halogen atom(s), a (C5-C10) cycloalkenyl substituted or not by one or more halogen atom(s), a (C8-C10) cycloalkynyl substituted or not by one or more halogen atom(s), a (C1-C10) alkoxy, a hydroxyl, a cyano, a nitro, a $NR_8R_{8'}$ (with $R_8$ and $R_{8'}$ as described above);

and any pharmaceutically acceptable salt, solvate, stereoisomers, diastereoisomers and enantiomers thereof or mixtures of stereoisomers, solvate or prodrug thereof.

2. A compound according to the claim 1 chosen from 2-(4-chlorophenylamino)-4-(4-tert-butylaminopiperidin-1-yl)-quinoline (1-5); 2-(4-chlorobenzylamino)-4-(4-tert-butylaminopiperidin-1-yl)-quinoline (2-2); 2-[3-methyl-4-(pyrimidin-2-ylamino)phenylamino]-4-(4-tert-butylaminopiperidin-1-yl)-quinoline (3-4); 2-{4-[4-(pyridin-3-yl)-2-pyrimidinamino]-3-methyl-phenylamino}-4-(4-tert-butylaminopiperidin-1-yl)-quinoline (4-2) or a pharmaceutically acceptable salt, solvate or prodrug thereof.

3. A compound according to the claim 1 chosen from 2-(4-chlorophenylamino)-4-(4-tert-butylaminopiperidin-1-yl)-quinoline hydrochloride salt (1-6); 2-(4-chlorobenzylamino)-4-(4-tert-butylaminopiperidin-1-yl)-quinoline hydrochloride salt (2-3); 2-[3-methyl-4-(pyrimidin-2-ylamino)phenylamino]-4-(4-tert-butylaminopiperidin-1-yl)-quinoline hydrochloride salt (3-5); 2-{4-[4-(pyridin-3-yl)-2-pyrimidinamino]-3-methyl-phenylamino}-4-(4-tert-butylaminopiperidin-1-yl)-quinoline hydrochloride salt (4-3) or a pharmaceutically acceptable solvate or prodrug thereof.

4. A pharmaceutical composition comprising a therapeutically effective amount of a compound according to claim 1, or a pharmaceutically acceptable salt, solvate or prodrug thereof, and a pharmaceutically acceptable adjuvant, diluent or carrier.

5. A pharmaceutical composition according to claim 4, further comprising in combination one or more anti-neoplastic agents.

6. A pharmaceutical composition according to claim 4, wherein the therapeutically effective amount of the compound is formulated or co-formulated in nanoparticles.

7. The pharmaceutical composition according to claim 6, wherein the nanoparticles comprise a polymeric biodegradable composition.

8. The pharmaceutical composition according to claim 7, wherein the polymer is based on Poly (DL-Lactic-co-glycolic acid) having molecular weight from 7 to 240 kDa; or a copolymer of polylactic acid (PLA) and polyglycolic acid (PGA) where the molecular ratio is between 95:5 and 50:50.

9. The pharmaceutical composition according to claim 6, wherein the nanoparticles comprise a lisosomal biodegradable composition.

10. The pharmaceutical composition according to claim 6, wherein the nanoparticles comprise a biocompatible polymer or copolymer.

11. The pharmaceutical composition according to claim 6, wherein the nanoparticles comprise a liposomal formulation.

12. The pharmaceutical composition according to claim 6, wherein the nanoparticles are associated covalently or non-covalently with a polyethylene glycol (PEG).

13. The pharmaceutical composition according to claim 6, wherein the nanoparticles have an average size of from about 80 to about 600 nm.

14. The pharmaceutical composition according to claim 6, wherein the compound is associated with at least one therapeutically active anticancer agent.

15. The pharmaceutical composition according to claim 1 which is suitable for oral-, parenteral-, ocular-, transdermal-, nasal-administration or for inhalation.

16. A pharmaceutical composition according to claim 6, wherein the nanoparticles comprise an item chosen from PLGA nanoparticules, PLGA-PEG nanoparticles (block type AB, BA, ABA or BAB, where A=PLGA and B=PEG) and targeted nanoparticules.

17. A pharmaceutical composition according to claim 16, wherein the nanoparticle is a targeted nanoparticle containing a signaling motif.

18. A pharmaceutical composition comprising a combination of a therapeutically effective amount of a compound according to claim 1 and a therapeutically effective amount of one or more anti-neoplastic agents, wherein the components constituting said combination are for simultaneous, separate or sequential use in cancer therapy.

19. The pharmaceutical composition of claim 5, wherein the anti-neoplastic agent is chosen from the group consisting of everolimus, chloroquine, hydroxychloroquine, trabectedin, abraxane, TLK 286, AV-299, DN-101, pazopanib, GSK690693, RTA 744, ON 0910.Na, ADZ-6244 (ARRY-142886), AMN-107, TKI-258, GSK461364, AZD 1152, enzastaurin, vandetanib, ARQ-197, MK-0457, MLN8054, PHA-739358, R-763, AT-9263, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, TNO 1001, IPdR1

KRX-0402, lucanthone, LY 317615, neuradiab, vitespan, Sdx 102, talampanel, atrasentan, Xr 311, romidepsin, ADS-100380, sunitinib, 5-fluorouracil, vorinostat, etoposide, gemcitabine, doxorubicin, irinotecan, liposomal doxorubicin, 5'-deoxy-5-fluorouridine, vincristine, temozolomide, ZK-304709, seliciclib, PD0325901, capecitabine, L-Glutamic acid, N-[4-[2-(2-amino-4,7-dihydro-4-oxo-1H-pyrrolo [2,3-d]pyrimidin-5-yl)ethyl]benzoyl]-disodium salt heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258, 3-[5-(methylsulfonylpiperadinemethyl)-indolyl-quinolone, vatalanib, AG-013736, AVE-0005, the acetate salt of [D-Ser(But)$_6$, Azglyi$_0$](pyro-Glu-His-Trp-Ser-Tyr-D-Ser(But)-Leu-Arg-Pro-Azgly-NH$_2$ acetate, goserelin acetate, leuprolide acetate, triptorelin pamoate, medroxyprogesterone acetate, hydroxyprogesterone caproate, megestrol acetate, raloxifene, bicalutamide, flutamide, nilutamide, CP-724714; TAK-165, HKI-272, lapatanib, canertinib, ABX-EGF antibody, erbitux, EKB-569, PM-166, GW-572016, lonafamib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, epirubicin, fludarabine, fludrocortisone, fluoxymesterone, gleevec, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, 1M862, angiostatin, vitaxin, droloxifene, spironolactone, finasteride, cimitidine, trastuzumab, denileukin diftitox, gefitinib, bortezimib, paclitaxel, docetaxel, bevacizumab (monoclonal antibody) and erbitux, cremophor-free paclitaxel, epithilone B, BMS-247550, BMS-310705, 4-hydroxytamoxifen, pipendoxifene, ERA-923, arzoxifene, fulvestrant, acolbifene, lasofoxifene, idoxifene, TSE-424, HMR-3339, ZK186619, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, nitrogen mustard, methylprednisolone, ibritgumomab tiuxetan, androgens, decitabine, hexamethylmelamine, bexarotene, tositumomab, arsenic trioxide, cortisone, editronate, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, prochlorperazine, granisetron, ondansetron, dolasetron, tropisetron, epoetin alfa and darbepoetin alfa, ipilumumab, vemurafenib, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, a mTOR inhibitor, an AKT inhibitor, a JAK/STAT inhibitor, a checkpoint-1 or 2 inhibitor, a focal adhesion kinase inhibitor, a Map kinase kinase (MEK) inhibitor, a VEGF trap antibody, and mixtures thereof.

20. The pharmaceutical composition according to claim 4, which is suitable for slow- or sustained-release.

21. A method for the treatment of a proliferative and/or neoplastic disease, comprising the step of administering a therapeutically active amount of a compound according to claim 1 to a human being or animal in need thereof.

22. A method for inhibiting the growth or differentiation of a Cancer Stem Cell (CSC), a tumor initiating cell, a mesenchymal-like cell associated with cancer, a mesenchymal cancerous cell, or a mesenchymal cell comprising the step of administering a therapeutically active amount of a compound according to claim 1, to a human being or an animal in need thereof.

23. A method for the treatment of a proliferative and/or neoplastic disease, comprising the step of administering a therapeutically active amount of a pharmaceutical composition according to claim 4, to a human being or animal in need thereof.

24. A method for inhibiting the growth or differentiation of a Cancer Stem Cell (CSC), a tumor initiating cell, a mesenchymal-like cell associated with cancer, a mesenchymal cancerous cell, or a mesenchymal cell comprising the step of administering a therapeutically active amount of a pharmaceutical composition according to claim 4, to a human being or an animal in need thereof.

* * * * *